United States Patent
Yang et al.

(10) Patent No.: US 9,421,276 B2
(45) Date of Patent: Aug. 23, 2016

(54) CLICKABLE POLYOXETANE CARRIER FOR DRUG DELIVERY

(71) Applicant: VIRGINIA COMMONWEALTH UNIVERSITY, Richmond, VA (US)

(72) Inventors: Hu Yang, Mechancsville, VA (US); Olga Zolotarskaya, Richmond, VA (US); Kenneth J. Wynne, Midlothian, VA (US); Kristoffer Valerie, Midlothian, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

(21) Appl. No.: 14/425,316

(22) PCT Filed: Sep. 3, 2013

(86) PCT No.: PCT/US2013/057874
§ 371 (c)(1),
(2) Date: Mar. 2, 2015

(87) PCT Pub. No.: WO2014/036566
PCT Pub. Date: Mar. 6, 2014

(65) Prior Publication Data
US 2015/0258204 A1    Sep. 17, 2015

Related U.S. Application Data

(60) Provisional application No. 61/695,927, filed on Aug. 31, 2012.

(51) Int. Cl.
C08G 63/91 (2006.01)
A61K 47/48 (2006.01)
C08G 65/18 (2006.01)
C08G 65/333 (2006.01)
A61K 31/4745 (2006.01)
C08G 65/32 (2006.01)

(52) U.S. Cl.
CPC ....... A61K 47/48215 (2013.01); A61K 31/4745 (2013.01); C08G 65/18 (2013.01); C08G 65/333 (2013.01); C08G 65/33396 (2013.01); C08G 2650/30 (2013.01); C08G 2650/60 (2013.01); C08L 2205/05 (2013.01)

(58) Field of Classification Search
CPC .............................. C07H 15/04; C08F 220/30
USPC ........ 525/326.6; 526/238.23, 277, 328.1, 328
See application file for complete search history.

(56) References Cited

U.S. PATENT DOCUMENTS

2011/0319569 A1 * 12/2011 Emrick ............ A61K 47/48176
525/326.6

* cited by examiner

*Primary Examiner* — Terressa Boykin
(74) *Attorney, Agent, or Firm* — Neifeld IP Law, PC

(57) ABSTRACT

A polymer is provided, comprising a subunit having the formula:

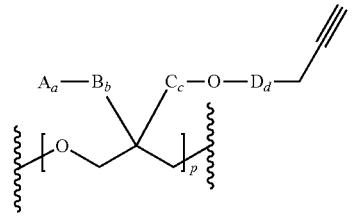

wherein A, B, C, D, a, b, c, d, and p are defined herein. Compositions, methods of making, and methods of use are provided.

18 Claims, 5 Drawing Sheets

CLICKABLE POLYOXETANE CARRIER FOR DRUG DELIVERY

REFERENCE TO AN EARLIER APPLICATION

This application claims priority to U.S. Provisional Application No. 61/695,927, filed Aug. 31, 2012.

GOVERNMENT LICENSE RIGHTS

This invention was made with government support under CBET0954957; DMR0802452; and DMR1206259 awarded by the National Science Foundation. The government has certain rights in the invention.

INTRODUCTION

1. Field of the Application

The present application relates to polyoxetanes, compositions containing same, methods of making, and their use.

2. Background

Covalently coupling anticancer drugs to polymeric carrier represents a viable approach to improving drug pharmacokinetic and pharmacodynamics. Camptothecin (CPT) is a potent and selective DNA topoisomerase I (TOP I) inhibitor, which binds to the TOP I and DNA through hydrogen bonds and stabilizes the enzyme-DNA complex that leads to DNA damage and subsequent cell apoptosis. CPT and its water soluble derivatives (e.g., irinotecan) can be used to treat many types of cancer such as brain cancer, colon cancer, and lung cancer. CPT possesses a planar pentacyclic ring structure and has low solubility in water. It exists in two forms—a therapeutically active lactone form and a therapeutically inactive carboxylate form.—Since the lactone form rapidly transforms into the carboxylate form at physiological pH, it is important to maintain CPT in the lactone form in drug-polymer coupling reactions and extend its stability with the use of polymeric carrier. Additionally, any inadvertent structural changes of the drug should be avoided to achieve expected therapeutic outcomes. The hydroxyl group of CPT is a primary site in CPT-polymer coupling reactions because chemical modification of CPT through alkylation or acylation of the hydroxyl group does not disrupt the lactone ring and indeed enhances its stability.

The hydroxyl group of CPT contributes to the stabilization of the TOP I and DNA complex via a hydrogen bond formed with the side chain on aspartic acid at position 533 (Asp533) of the enzyme. To fully recover the biological activity of the drug, a cleavable linkage, typically an ester bond, connecting the drug to the polymer via the hydroxyl group is commonly used. CPT has been previously used as an initiator to polymerize D, L-lactide and obtained CPT-terminated polylactide.—CPT-polylactide conjugates were formulated into nanoparticles. However, the release of CPT from this system still relies on hydrolytic cleavage of ester bond. In some systems, CPT is coupled to the carrier through a heterobifunctional spacer to utilize highly efficient controlled synthesis such as click chemistry. Copper (I)-catalyzed azide-alkyne cycloaddition (CuAAC) click chemistry yields high coupling efficiency and allows precise control of compositions and functionalization. Therefore CuAAC click chemistry has attracted considerable attention in drug delivery. For example, Parrish and Emrick modified CPT with an azide-containing spacer and click coupled it to an acetylene functionalized copolymer made from α-propargyl-δ-valerolactone and ε-caprolactone monomers.

Polymeric carriers have been adopted widely as an important class of vehicles for delivery of drugs and imaging agents. An ideal carrier is expected to possess not only biologically favorable properties such as non-toxicity and non-immunogenicity but a high cargo capacity. In the covalent approach, efficient and controlled coupling reactions are crucial for success of drug coupling and functionalization of the delivery system.

BRIEF DESCRIPTION OF THE SEVERAL EMBODIMENTS

Figure 1:
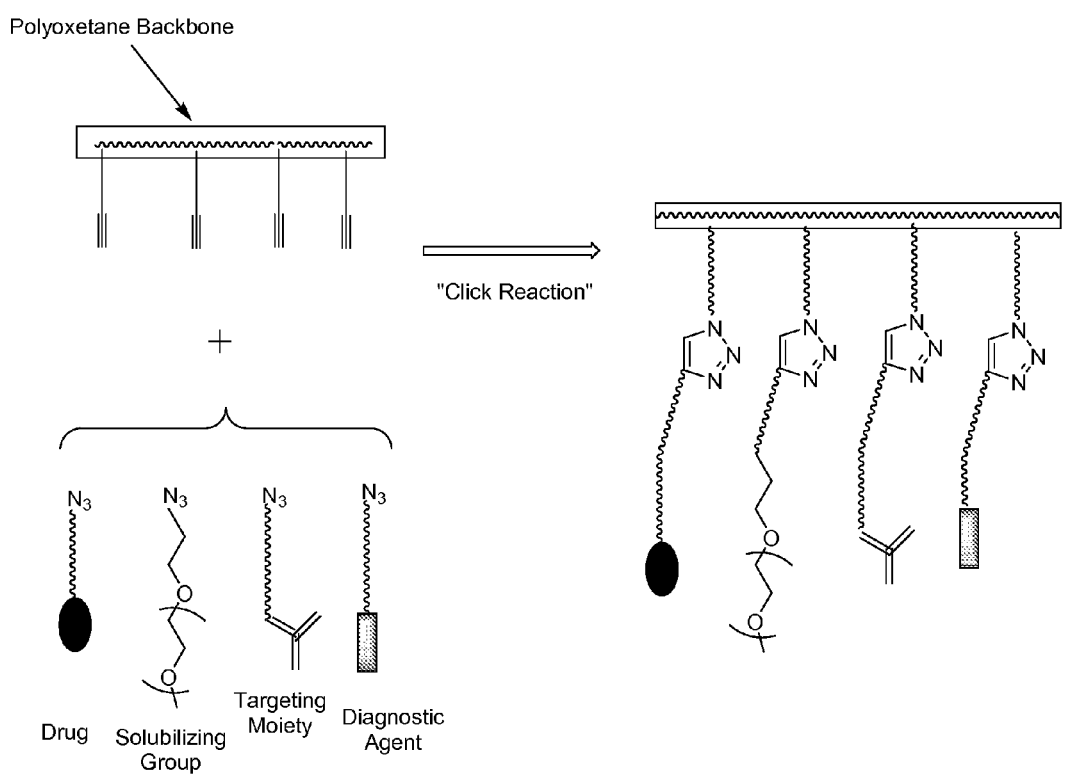
FIG. 1: Simple representation of an exemplary embodiment.

One embodiment provides a polymer, comprising a subunit having the formula:

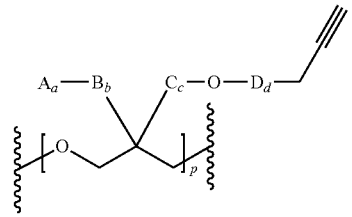

wherein:

A is independently hydrogen, $C_{1-10}$ alkyl, $C_{3-10}$ alkenyl, $C_{3-10}$ alkynyl, $C_{3-20}$ cycloalkyl, $C_{5-20}$ cycloalkenyl, $C_{5-25}$ aryl, —$OR^1$, —$COOR^1$, —$C(O)R^1$, —C(O)-halogen, —$SR^1$, —$OSO_2R^1$, —$CONR^1R^2$, —$NR^1R^2$, —$N_3$, or halogen;

B is independently $C_{1-10}$ alkylene, $C_{3-10}$ alkenylene, $C_{3-10}$ alkynylene, $C_{3-20}$ cycloalkylene, $C_{5-20}$ cycloalkenylene, $C_{5-25}$ arylene, —COO—, —C(O)—, —S—, —$CONR^1$—, —$NR^1$—, —$CH_2CH_2O$—, —O—, or combination of two or more of the foregoing;

C is independently $C_{1-10}$ alkylene, $C_{3-10}$ alkenylene, $C_{3-10}$ alkynylene, $C_{3-20}$ cycloalkylene, $C_{5-20}$ cycloalkenylene, $C_{5-25}$ arylene, —COO—, —C(O)—, —S—, —$CONR^1$—, —$NR^1$—, —$CH_2CH_2O$—, —O—, or combination of two or more of the foregoing;

D is independently $C_{1-10}$ alkylene, $C_{3-10}$ alkenylene, $C_{3-10}$ alkynylene, $C_{3-20}$ cycloalkylene, $C_{5-20}$ cycloalkenylene, $C_{5-25}$ arylene, —COO—, —C(O)—, —S—, —$CONR^1$—, —$NR^1$—, —$CH_2CH_2O$—, —O—, or combination of two or more of the foregoing;

a is 1;
b is independently 0-10;
c is independently 1-20;
d is independently 0-20;
p is greater than 0;

$R^1$ and $R^2$ are independently hydrogen, $C_{1-10}$ alkyl, $C_{3-10}$ alkenyl, $C_{3-10}$ alkynyl, $C_{3-20}$ cycloalkyl, $C_{5-20}$ cycloalkenyl, or $C_{5-25}$ aryl;

and wherein one or more of the alkyl, alkenyl, alkynyl, cycloalkyl, cycloalkenyl, aryl, alkylene, alkenylene, alkynylene, cycloalkylene, cycloalkenylene, and arylene may independently be branched, unbranched, unsubstituted, substituted, or contain at least one heteroatom.

As used herein, the $C_{1-10}$ alkyl can have 1, 2, 3, 4, 5, 6, 7, 8, 9, or 10 carbons.

As used herein, the $C_{3-10}$ alkenyl can have 3, 4, 5, 6, 7, 8, 9, or 10 carbons.

As used herein, the $C_{3-10}$ alkynyl can have 3, 4, 5, 6, 7, 8, 9, or 10 carbons.

As used herein, the $C_{3-20}$ cycloalkyl can have 3, 4, 5, 6, 7, 8, 9, 10, 11, 12, 13, 14, 15, 16, 17, 18, 19, or 20 carbons.

As used herein, the $C_{5-20}$ cycloalkenyl can have 5, 6, 7, 8, 9, 10, 11, 12, 13, 14, 15, 16, 17, 18, 19, or 20 carbons.

As used herein, the $C_{5-25}$ aryl can have 5, 6, 7, 8, 9, 10, 11, 12, 13, 14, 15, 16, 17, 18, 19, 20, 21, 22, 23, 24, or 25 carbons.

As used herein, the halogen can be F, Cl, Br or I.

As used herein, the $C_{1-10}$ alkylene can have 1, 2, 3, 4, 5, 6, 7, 8, 9, or 10 carbons.

As used herein, the $C_{3-10}$ alkenylene can have 3, 4, 5, 6, 7, 8, 9, or 10 carbons.

As used herein, the $C_{3-10}$ alkynylene can have 3, 4, 5, 6, 7, 8, 9, or 10 carbons.

As used herein, the $C_{3-20}$ cycloalkylene can have 3, 4, 5, 6, 7, 8, 9, 10, 11, 12, 13, 14, 15, 16, 17, 18, 19, or 20 carbons.

As used herein, the $C_{5-20}$ cycloalkenylene can have 5, 6, 7, 8, 9, 10, 11, 12, 13, 14, 15, 16, 17, 18, 19, or 20 carbons.

As used herein, the $C_{5-25}$ arylene can have 5, 6, 7, 8, 9, 10, 11, 12, 13, 14, 15, 16, 17, 18, 19, 20, 21, 22, 23, 24, or 25 carbons.

As used herein, the $C_{1-10}$ alkylene can have 1, 2, 3, 4, 5, 6, 7, 8, 9, or 10 carbons.

As used herein, the $C_{3-10}$ alkenylene can have 3, 4, 5, 6, 7, 8, 9, or 10 carbons.

As used herein, the $C_{3-10}$ alkynylene can have 3, 4, 5, 6, 7, 8, 9, or 10 carbons.

As used herein, the $C_{3-20}$ cycloalkylene can have 3, 4, 5, 6, 7, 8, 9, 10, 11, 12, 13, 14, 15, 16, 17, 18, 19, or 20 carbons.

As used herein, the $C_{5-20}$ cycloalkenylene can have 5, 6, 7, 8, 9, 10, 11, 12, 13, 14, 15, 16, 17, 18, 19, or 20 carbons.

As used herein, the $C_{5-25}$ arylene can have 5, 6, 7, 8, 9, 10, 11, 12, 13, 14, 15, 16, 17, 18, 19, 20, 21, 22, 23, 24, or 25 carbons.

As used herein, the $C_{1-10}$ alkylene can have 1, 2, 3, 4, 5, 6, 7, 8, 9, or 10 carbons.

As used herein, the $C_{3-10}$ alkenylene can have 3, 4, 5, 6, 7, 8, 9, or 10 carbons.

As used herein, the $C_{3-10}$ alkynylene can have 3, 4, 5, 6, 7, 8, 9, or 10, 11, 12, 13, 14, 15, 16, 17, 18, 19, 20, 21, 22, 23, 24, 25 carbons.

As used herein, the $C_{3-20}$ cycloalkylene can have 3, 4, 5, 6, 7, 8, 9, 10, 11, 12, 13, 14, 15, 16, 17, 18, 19, or 20 carbons.

As used herein, the $C_{5-20}$ cycloalkenylene can have 5, 6, 7, 8, 9, 10, 11, 12, 13, 14, 15, 16, 17, 18, 19, or 20 carbons.

As used herein, the $C_{5-25}$ arylene can have 5, 6, 7, 8, 9, 10, 11, 12, 13, 14, 15, 16, 17, 18, 19, 20, 21, 22, 23, 24, or 25 carbons.

As used herein, the b can be 0, 1, 2, 3, 4, 5, 6, 7, 8, 9, or 10.

As used herein, the c can be 1, 2, 3, 4, 5, 6, 7, 8, 9, 10, 11, 12, 13, 14, 15, 16, 17, 18, 19, or 20.

As used herein, the d can be 0, 1, 2, 3, 4, 5, 6, 7, 8, 9, 10, 11, 12, 13, 14, 15, 16, 17, 18, 19, or 20.

As used herein, the p is greater than 0, which can include 1, 2, 3, 4, 5, 6, 7, 8, 9, 10, 20, 25, 30, 35, 40, 45, 50, 75, 100, 200, 500, 750, 1000, or more. In one embodiment, p is 5-1000.

In one embodiment, p is 25-120.

In one embodiment, one or more of the alkyl, alkenyl, alkynyl, cycloalkyl, cycloalkenyl, aryl, alkylene, alkenylene, alkynylene, cycloalkylene, cycloalkenylene, and arylene may independently be branched, unbranched, unsubstituted, substituted, or contain at least one heteroatom. Such substituents and heteroatoms are easily determined by the skilled artisan. Nonlimiting examples of heteroatoms include N, O, and S, for example, which may replace one or more carbons.

As used herein, the term, subunit, is intended to mean a polymerized or polymerizable group such as a monomer, for example, which is or can be chemically bonded to one or more adjoining groups as is known in polymer chemistry. The adjoining groups can have the same or different structure as the subunit, e.g., an end group, co-monomer, n-mer, oligomer, or the like.

In one embodiment of the foregoing polymer, the polymer has the formula:

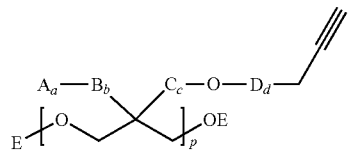

wherein E is hydrogen or $-C(O)CH=CH_2$.

In one embodiment, A is $-CH_3$, B is $-CH_2-$, and C is $-CH_2-$; a, b and c are 1; and d is 0.

As used herein, E is hydrogen or $-C(O)CH=CH_2$. In one embodiment, E is hydrogen.

One embodiment provides a polymer, comprising a subunit having the formula:

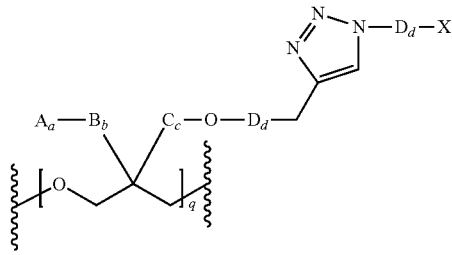

wherein A, B, C, D, a, b, c, d, $R^1$ and $R^2$ are as defined above; q is greater than 0; and X is A, pharmaceutically active agent, physiological targeting agent, diagnostic agent, or combination of two or more of the foregoing.

In one embodiment of the foregoing polymer, the polymer has the formula:

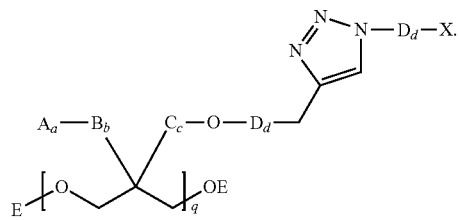

As used herein, the q is greater than 0, which can include 1, 2, 3, 4, 5, 6, 7, 8, 9, 10, 20, 25, 30, 35, 40, 45, 50, 75, 100, 200, 500, 750, 1000, or more. In one embodiment, q is 5-1000. In one embodiment, q is 25-120.

In one embodiment, the pharmaceutically active agent is docetaxel, gemcitabine, epirubicin, paclitaxel, geldanamycin, doxorubicin, camptothecin, topotecan, irinotecan, 9-aminocaptothecin, fluorouracil, platinate, cisplatin, carboplatin, DACH-Pt, anti-angiogenic drug, anti-fibrotic agent, therapeutic sensitizer, ATM kinase inhibitor, phosphatidylinositol 3-kinase/protein kinase, ATR kinase, DNA-PKcs kinase, CNS-active agent, cardio-vascular drug, immune-stimulating drug, antimicrobial agent, antiparasitic agent, anti-inflammatory agent, analgesic, anesthetic, or combination of two or more thereof.

In one embodiment, the pharmaceutically active agent is camptothecin.

In one embodiment of the foregoing polymer, the subunit has one of the following formulas:
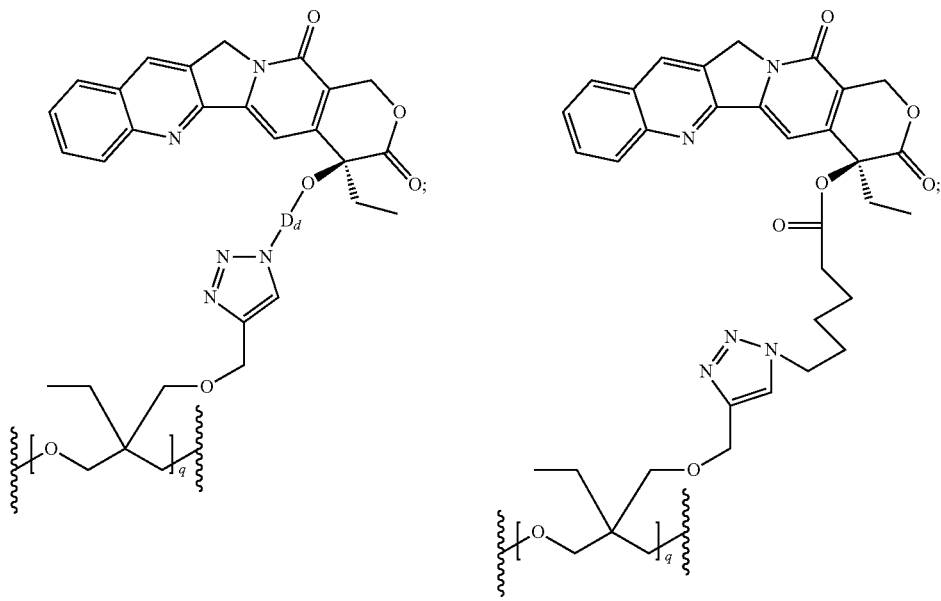
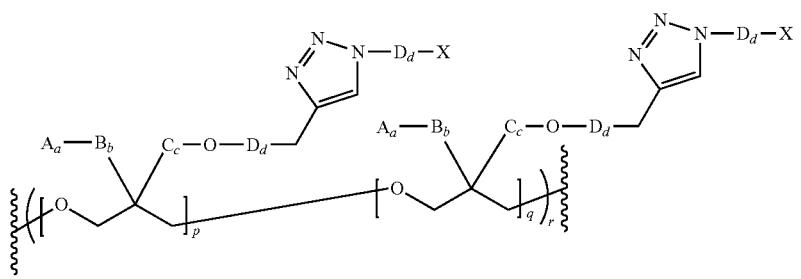
wherein p, q and r are greater than 0;
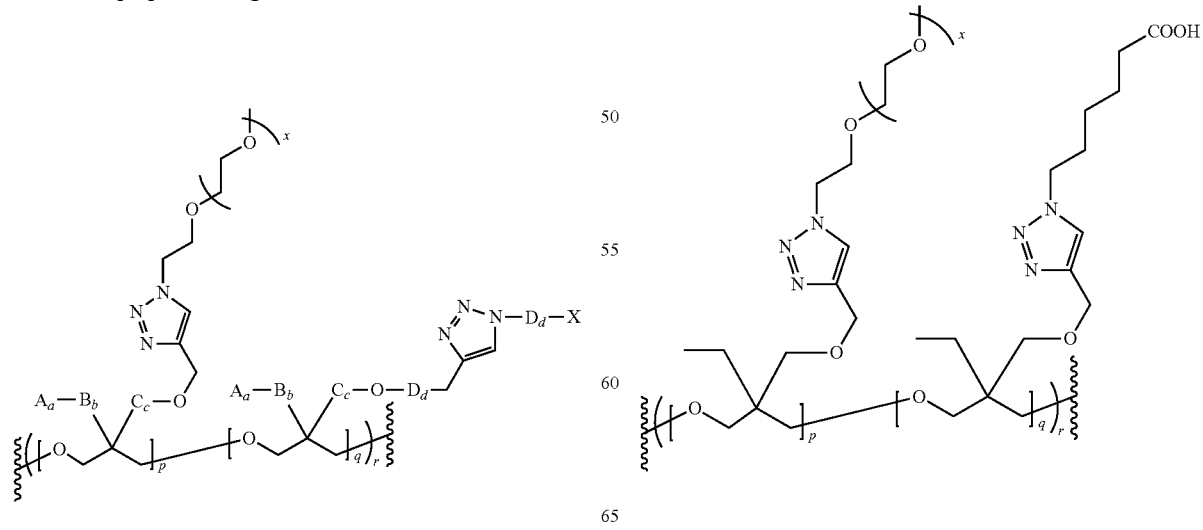
wherein p, q, r and x are greater than 0;
wherein p, q, r and x are greater than 0;

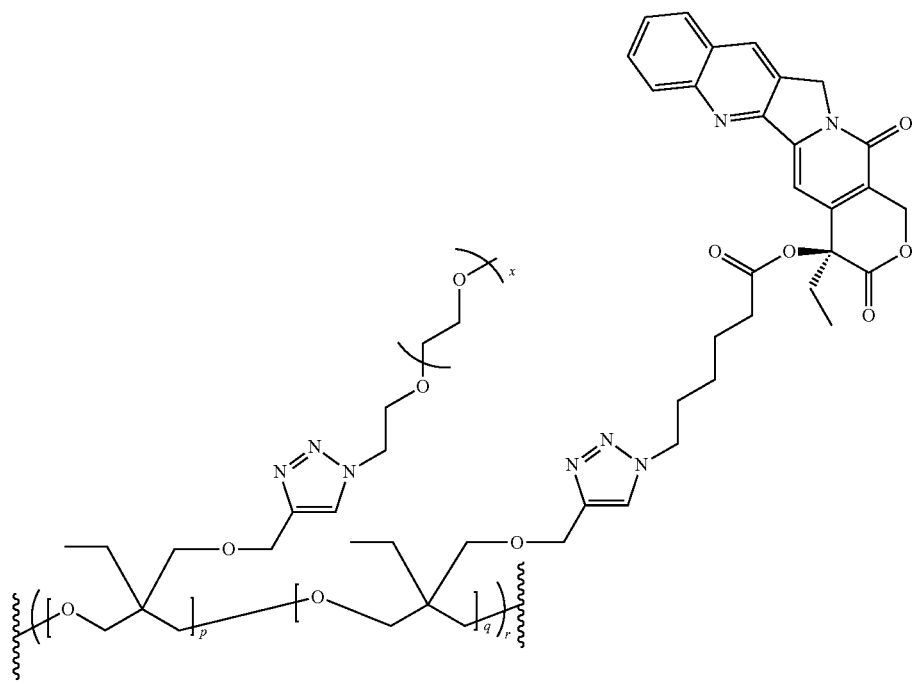
wherein p, q, r and x are greater than 0;
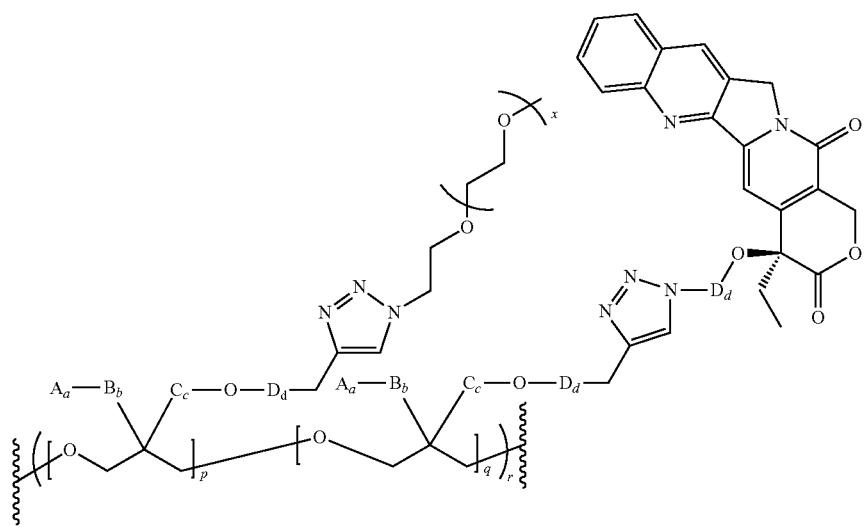
wherein p, q, r and x are greater than 0;

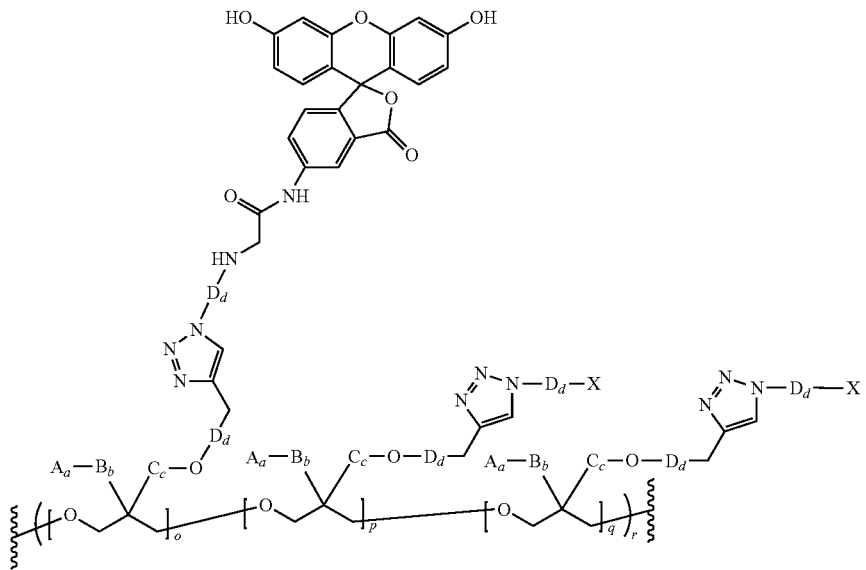
wherein o, p, q, and r are greater than 0;
or
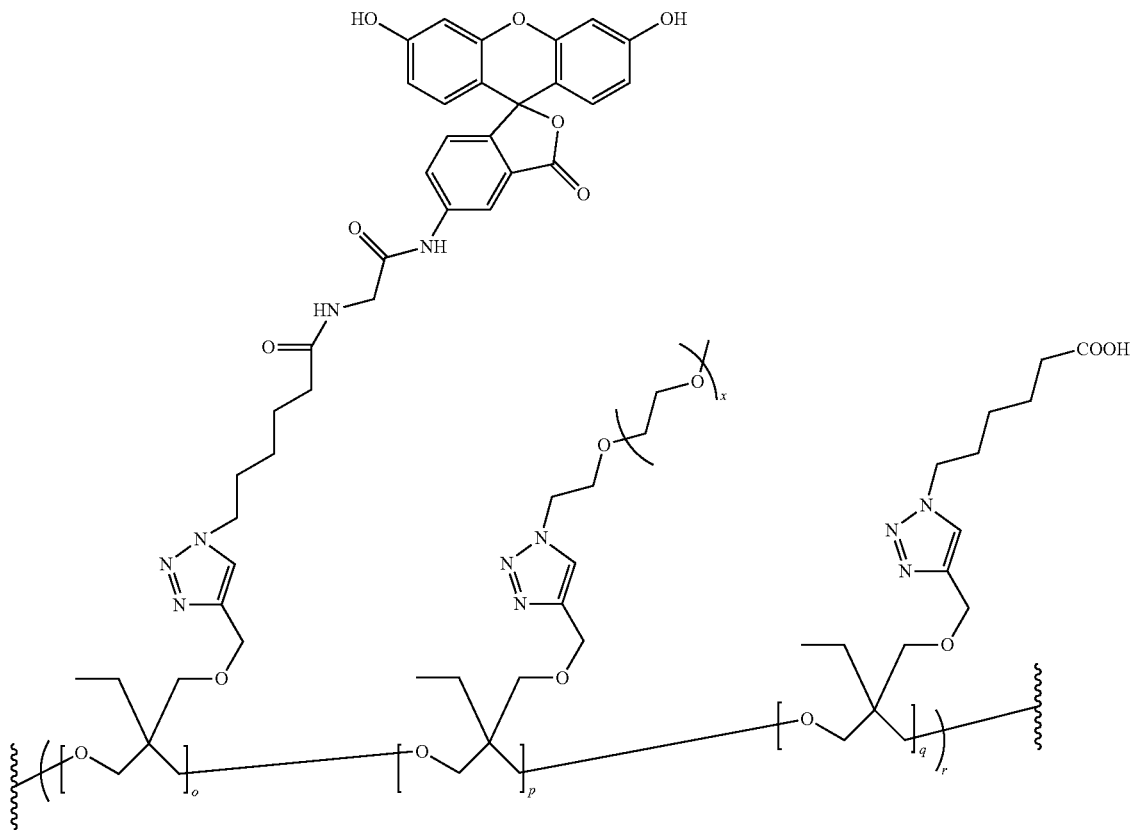
wherein o, p, r and x are greater than 0.

In one embodiment of the foregoing polymer, the polymer has one of the following formulas:
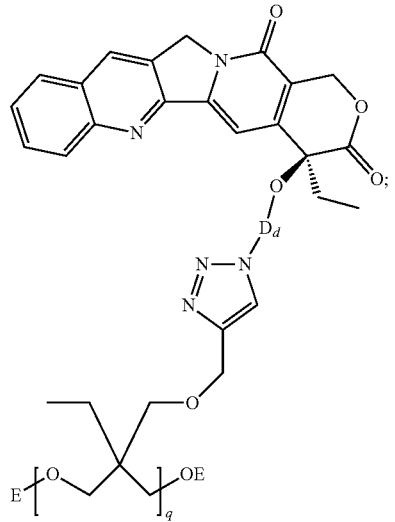
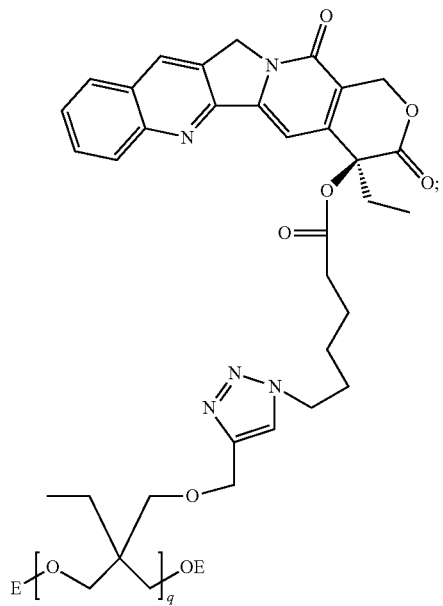
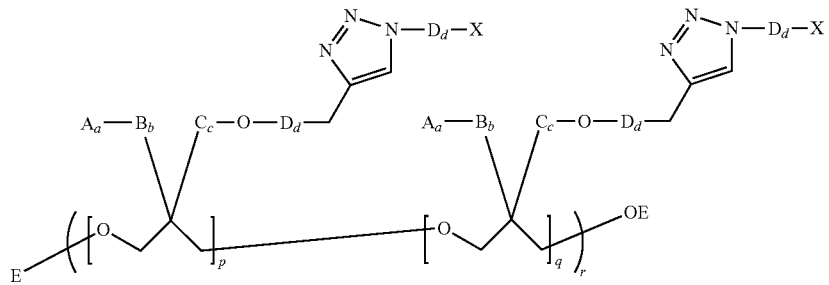
wherein p, q and r are greater than 0;

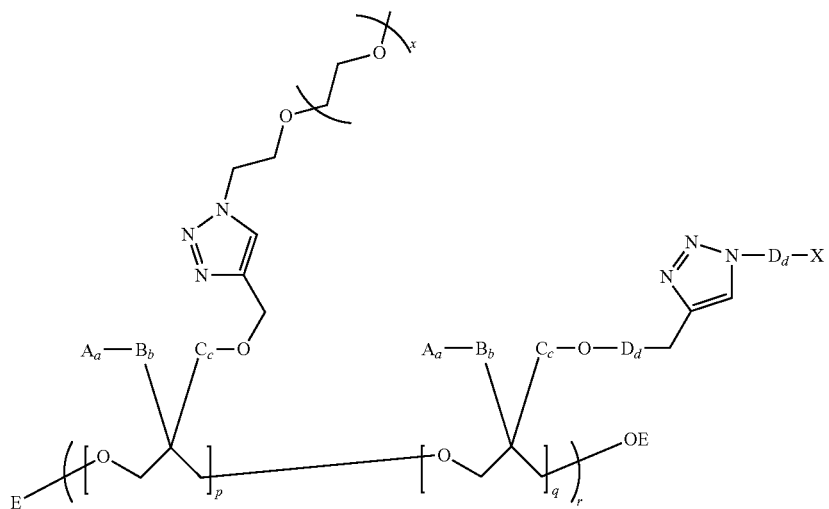
wherein p, q, r and x are greater than 0;
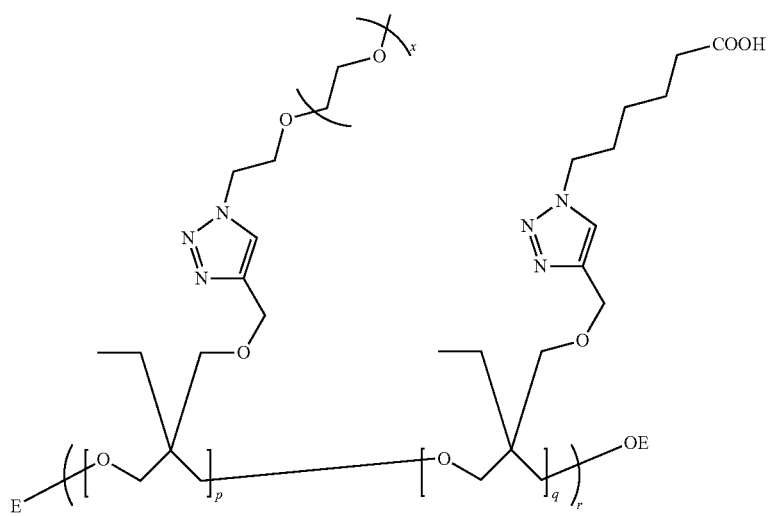
wherein p, q, r and x are greater than 0;

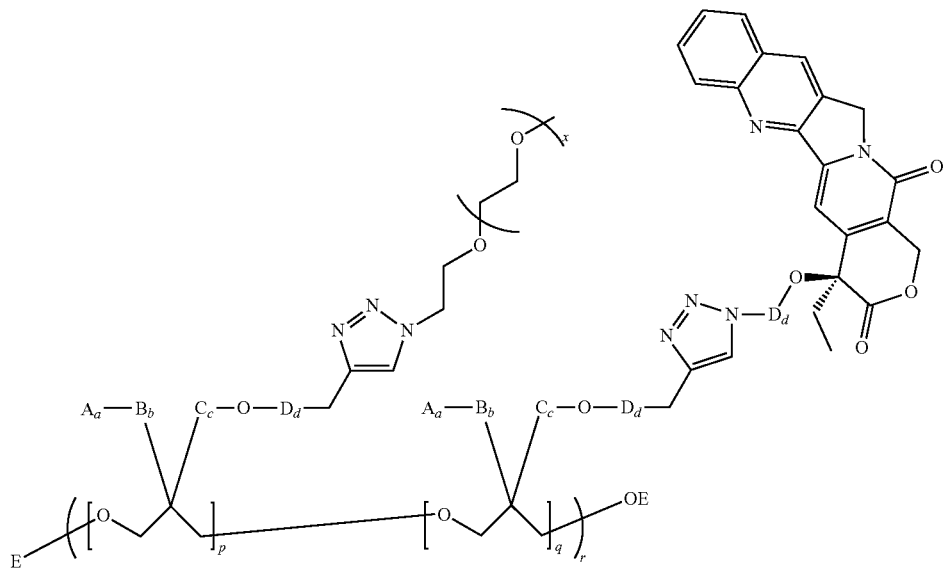
wherein p, q, r and x are greater than 0;
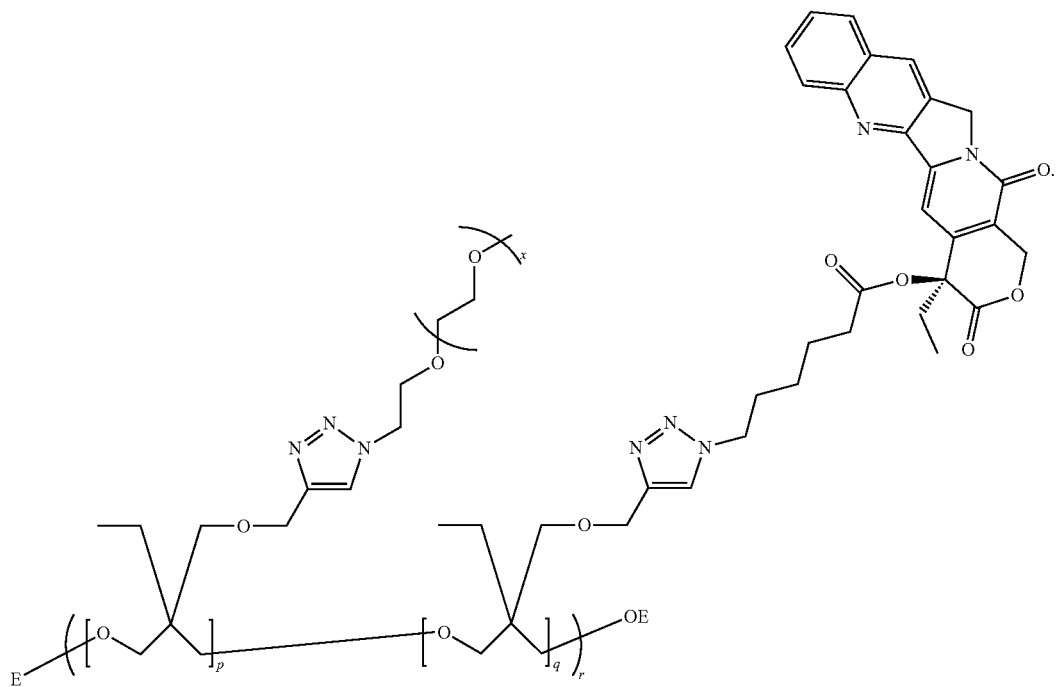
wherein p, q, r and x are greater than 0;

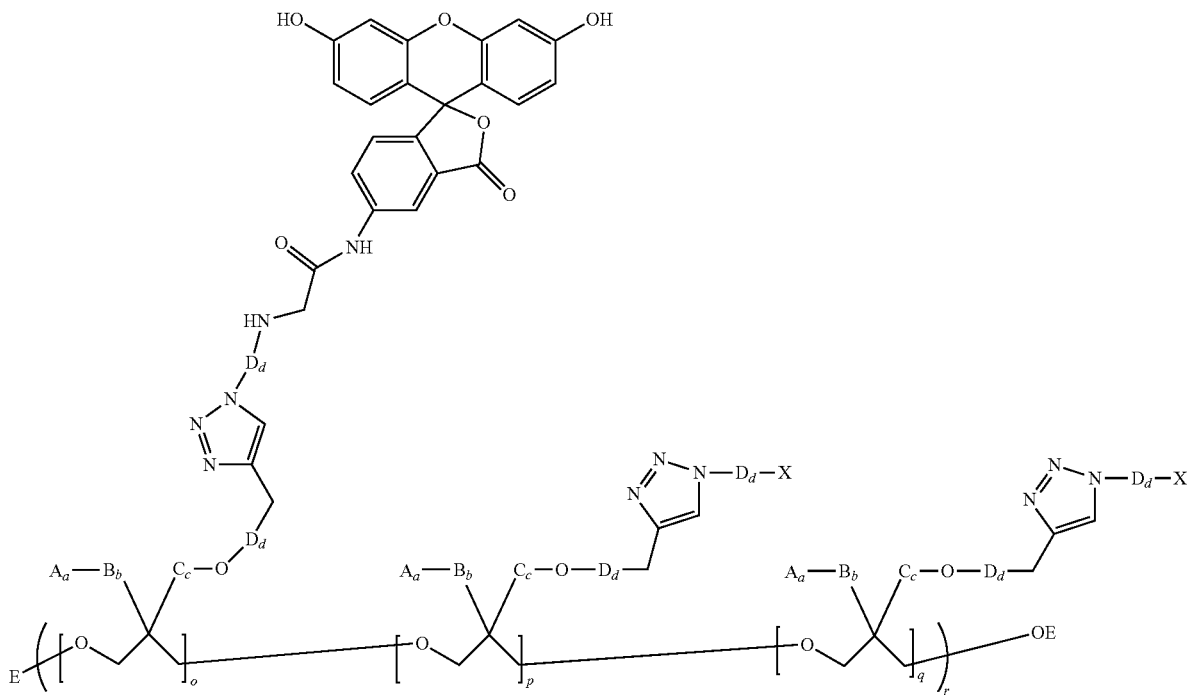
30
wherein o, p, q, and r are greater than 0;
or
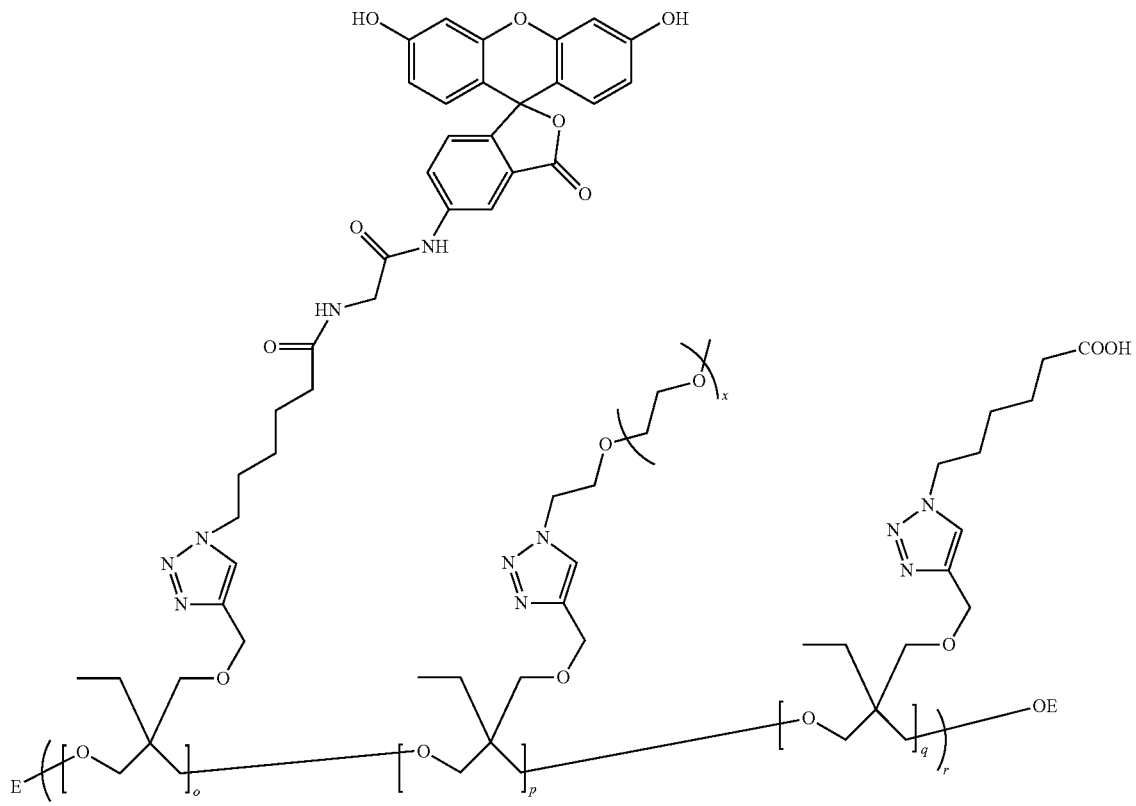
wherein o, p, r and x are greater than 0.

As used herein, the o is greater than 0, which can include 1, 2, 3, 4, 5, 6, 7, 8, 9, 10, 20, 25, 30, 35, 40, 45, 50, 75, 100, 200, 500, 750, 1000, or more. In one embodiment, o is 5-1000. In one embodiment, o is 25-120.

As used herein, the r is greater than 0, which can include 1, 2, 3, 4, 5, 6, 7, 8, 9, 10, 20, 25, 30, 35, 40, 45, 50, 75, 100, 200, 500, 750, 1000, or more. In one embodiment, r is 5-1000. In one embodiment, r is 25-120.

As used herein, x is greater than 0, which can include 1, 2, 3, 4, 5, 6, 7, 8, 9, 10, 20, 25, 30, 35, 40, 45, 50, 55, 60, 65, 70, 75, 80, 85, 90, 95, 100, 200, 500, 750, 1000, or more. In one embodiment, x is 1-100. In one embodiment, x is 5-75. In one embodiment, x is 1-15.

One embodiment provides a composition, comprising one or more of any of the polymers herein. In one embodiment, the composition is a physiological or pharmaceutical composition suitable for administration to a living subject, such as a human or animal. In one embodiment, the composition includes a physiologically or pharmaceutically acceptable carrier, such as water, physiological saline, or the like.

One embodiment provides a method for treating cancer in a subject in need thereof, comprising administering to said subject an effective amount of a polymer comprising a subunit having the following formula:

In one embodiment, the cancer is brain cancer, colon cancer, lung cancer, breast cancer, liver cancer, kidney cancer, melanoma, non-Hodgkin lymphoma, pancreatic cancer, prostate cancer, thyroid cancer, leukemia, endometrial cancer, ocular cancer, bladder cancer, head and neck cancer, astrocytoma, ependymoma, mixed glioma, oligoastrocytoma, oligodendroglioma, optic glioma, gliomatosis cerebri, glioblastoma multiforme, metastasized forms thereof, or combination thereof.

By effective amount it is meant an amount of the polymer that is sufficient in one or more administrations to reduce or ameliorate the symptoms of the underlying malady, e.g., cancer, or reduce or ameliorate the underlying malady itself. The administration route is not particularly limited, and may include oral, intravenous, parenteral, or the like. The effective amount and administration route can be easily determined by the attending physician or clinician.

One embodiment provides a method for selectively inhibiting DNA topoisomerase I, comprising contacting a polymer comprising a subunit having the following formula:

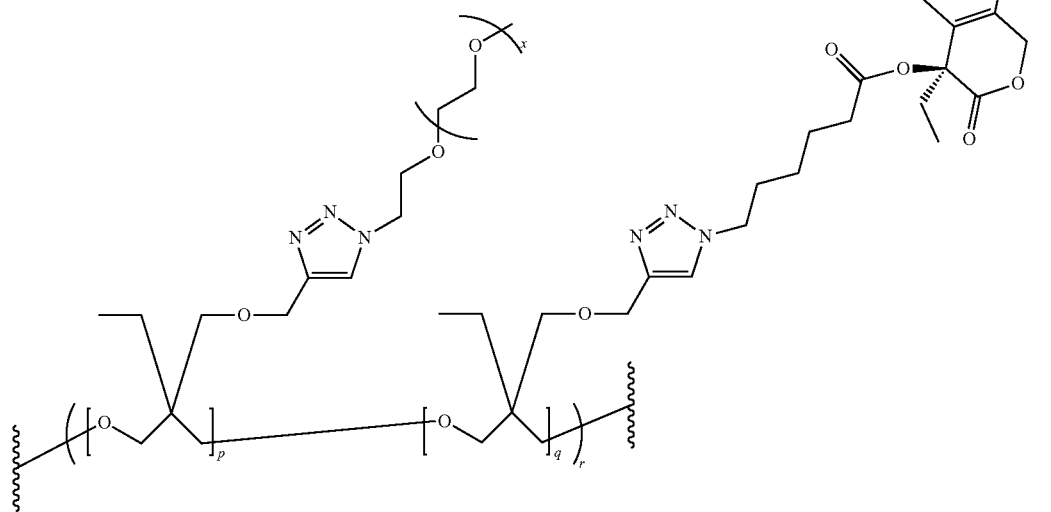

wherein p, q, r and x are greater than 0.

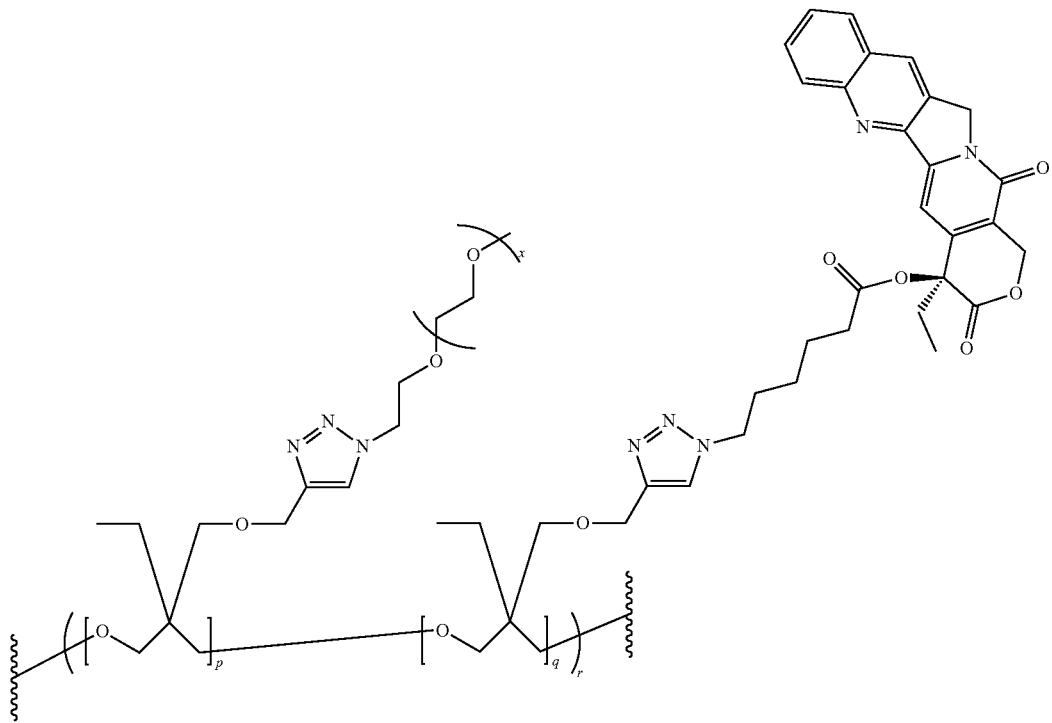
wherein p, q, r and x are greater than 0;
with the DNA topoisomerase I.
The DNA topoisomerase I may be present in vitro or in vivo. In one embodiment, the DNA topoisomerase I is present in a human subject.
In one embodiment of the foregoing treating and inhibiting methods, the polymer has the formula:
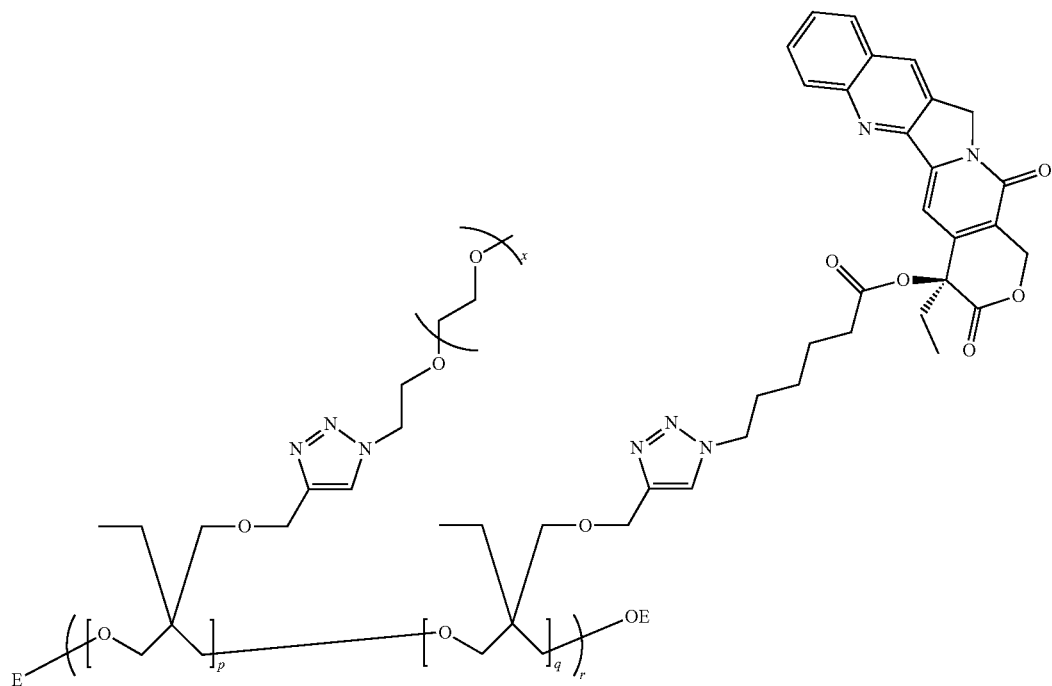

wherein p, q, r, x and E are as defined above. In one embodiment, E is hydrogen.

One embodiment provides a polymer, comprising a subunit having the formula:

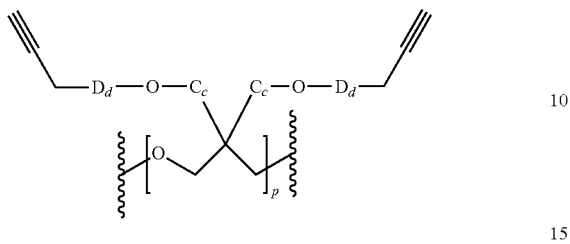

wherein C, D, c, d, p, and $R^1$ are as defined above.

One embodiment provides a polymer, comprising a subunit having the formula:

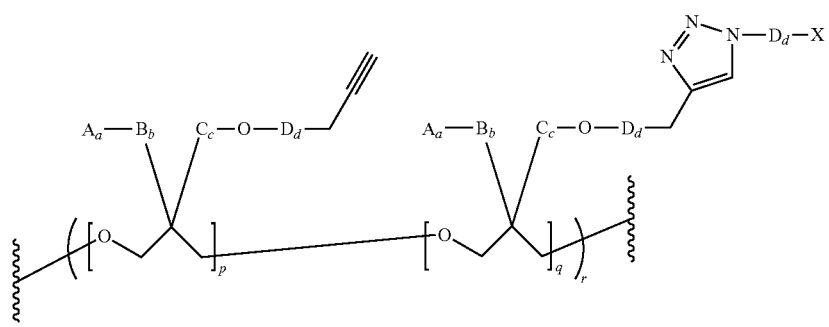

wherein A, B, C, D, a, b, c, d, p, q, r, $R^1$, $R^2$, and X are as defined above.

In one embodiment of the foregoing polymer, the subunit has the formula:

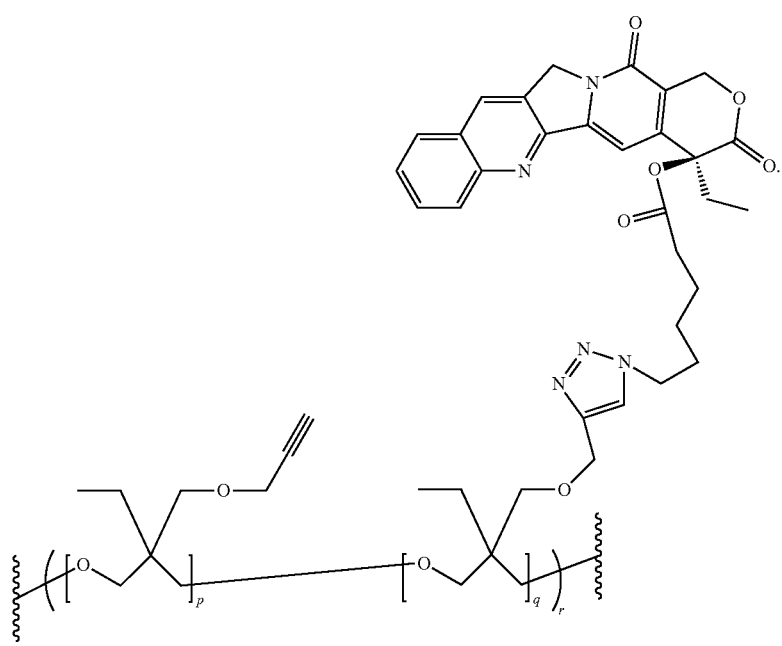

In one embodiment of the foregoing polymer, the polymer has the formula:

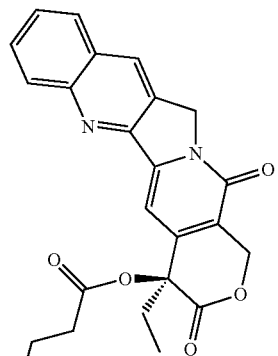
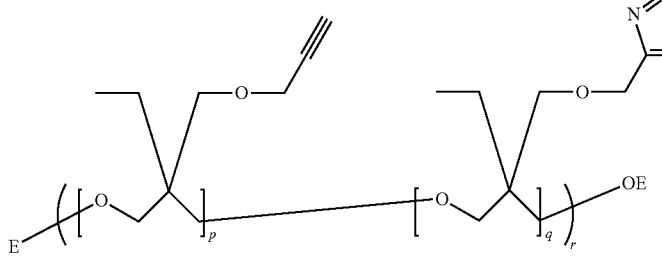

wherein E is defined above.

One embodiment provides a method for synthesis, comprising a reaction of a compound having the formula:

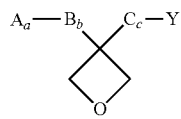

and a compound having the formula:

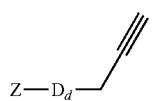

to produce a compound having the formula:

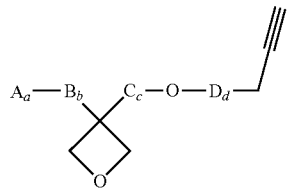

wherein A, B, C, D, a, b, c, and d are as defined above; Y is —OH, halo, or —OSO$_2$R$^1$, and Z is —OH, halo, or —OSO$_2$R$^1$ with the proviso that at least one of Y and Z, but not both, is —OH; and R$^1$ is defined as above.

As used herein, the halo for Y and Z may be Br, I, or Cl.

In one embodiment of the foregoing method, the reaction may be carried out using, for example, NaH and THF.

In one embodiment, the compound having the formula:

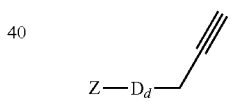

has one of the following formulas:

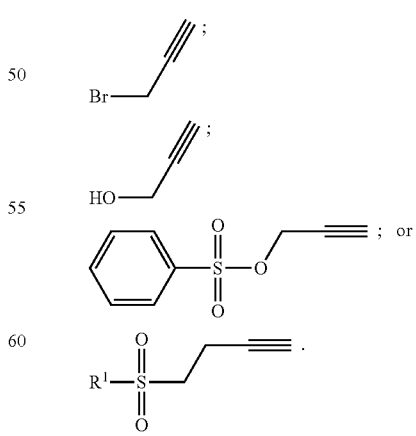

One embodiment provides a method for synthesis, comprising polymerizing a compound having the formula:

to produce a polymer comprising a subunit having the formula:

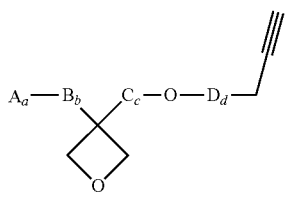

wherein A, B, C, D, a, b, c, d, and p are as defined above.

In one embodiment of the foregoing polymerization, the polymer has the formula:

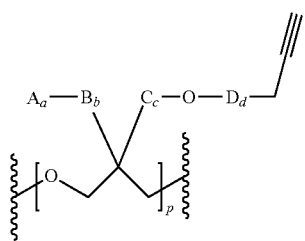

One embodiment provides a method for synthesis, comprising polymerizing a compound having the formula:

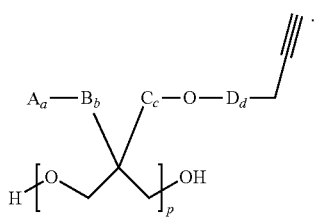

to produce a polymer comprising a subunit having the formula:

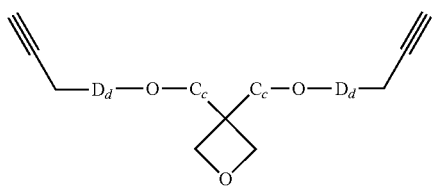

wherein C, D, c, d, and p are as defined above.

In one embodiment of the foregoing method, the polymer has the formula:

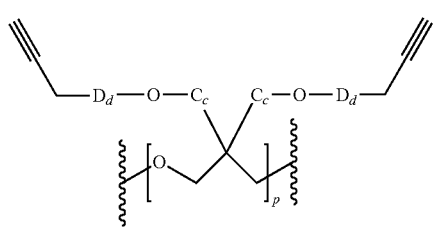

In one embodiment, C is —$CH_2$—; c is 1; and d is 0.

In one embodiment of the foregoing methods, the polymerization may be suitably carried out using, for example, BTDE/BD and DCM.

One embodiment provides a method for synthesis, comprising a reaction of a first polymer comprising a subunit having the formula:

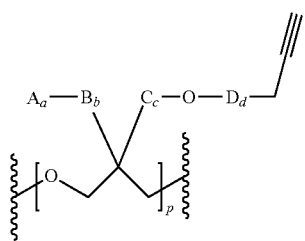

and a compound having the formula:

$N_3$-$D_d$-X to produce a second polymer, comprising a subunit having the formula:

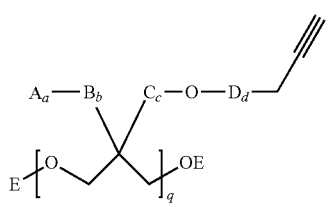

wherein A, B, C, D, a, b, c, d, p, q, and X are as defined above.

In one embodiment of the foregoing method, the reaction may be suitably carried out using the "click" reaction, for example, with CuI/PMDTA/THF, CuBr/bi-Py/DMSO, and the like.

In one embodiment of the foregoing method, the first polymer has the formula:

In one embodiment of the foregoing method, the second polymer has the formula:

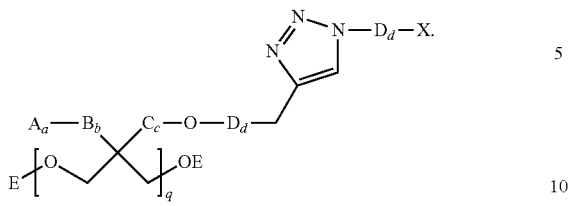

One embodiment provides a method for synthesis, comprising a reaction of a first polymer comprising a subunit having the formula:

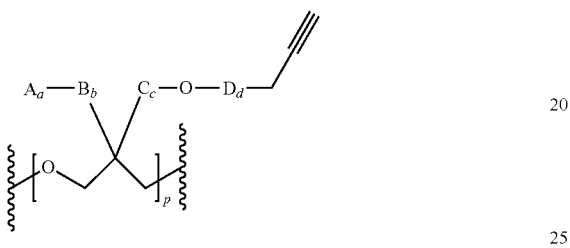

and a compound having the formula:

$N_3$-$D_d$-X to produce a second polymer comprising a subunit having the formula:

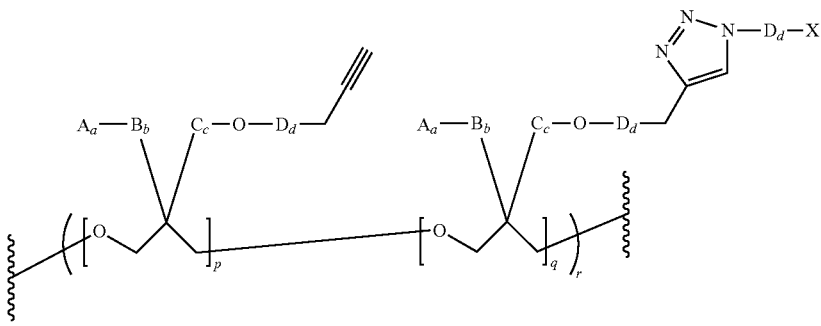

wherein A, B, C, D, a, b, c, d, p, q, r, and X are as defined above.

In one embodiment of the foregoing method, the reaction may be suitably carried out using the "click" reaction, for example, with CuI/PMDTA/THF, CuBr/bi-Py/DMSO, and the like.

In one embodiment of the foregoing method, the first polymer has the formula:

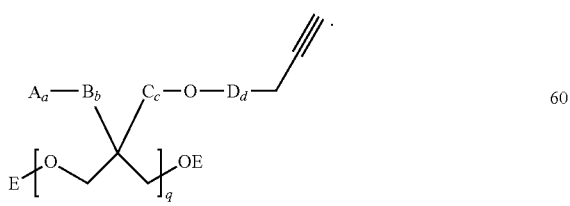

In one embodiment of the foregoing method, the second polymer has the formula:

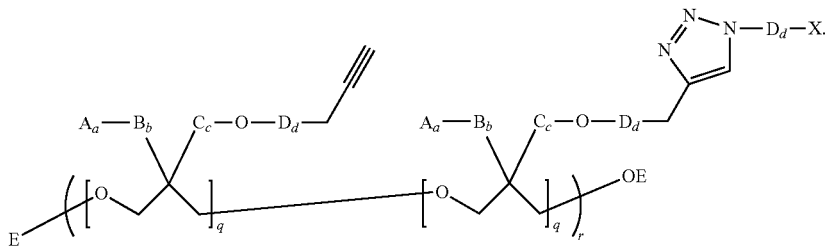
In one embodiment of the foregoing method, the second polymer has the formula:
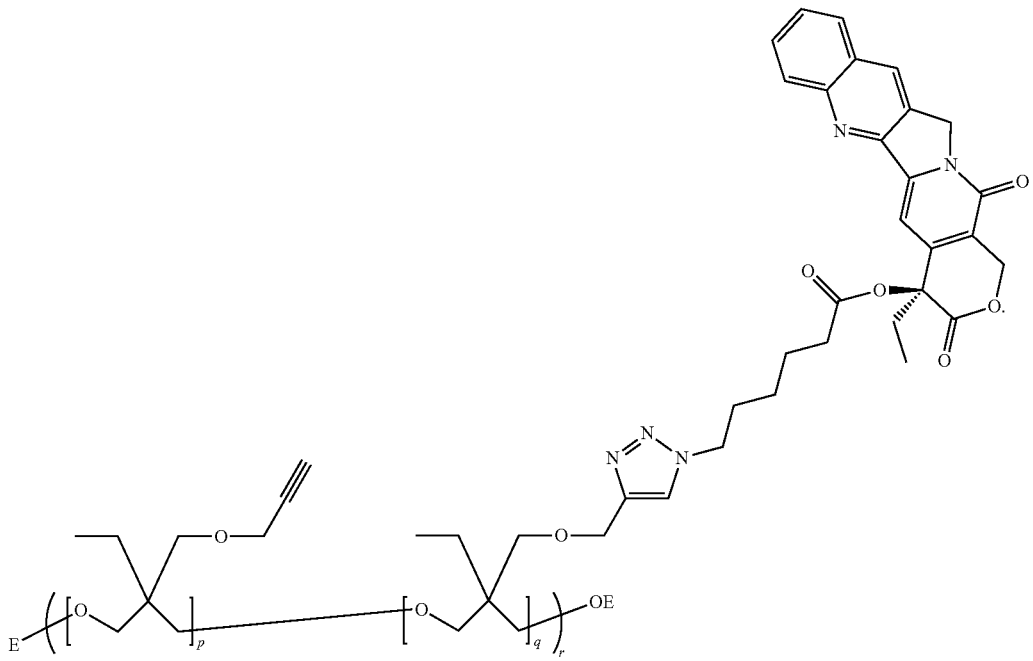
In one embodiment of the foregoing method, the second polymer has the formula:
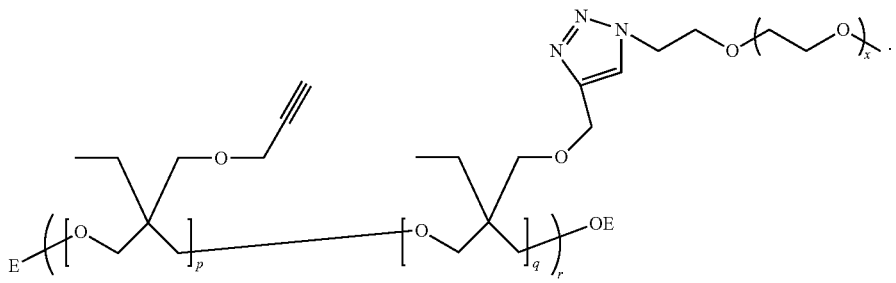
One embodiment provides a method for synthesis, comprising a reaction of a first polymer comprising a subunit having the formula:

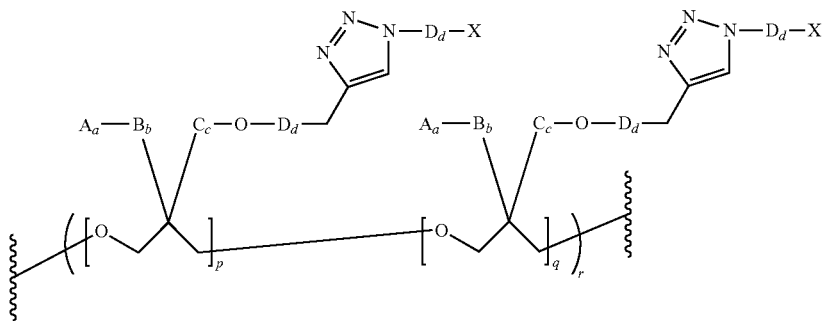
and a compound having the formula:
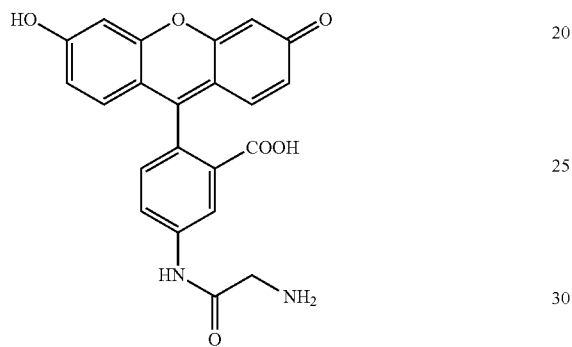
to produce a second polymer comprising a subunit having the formula:
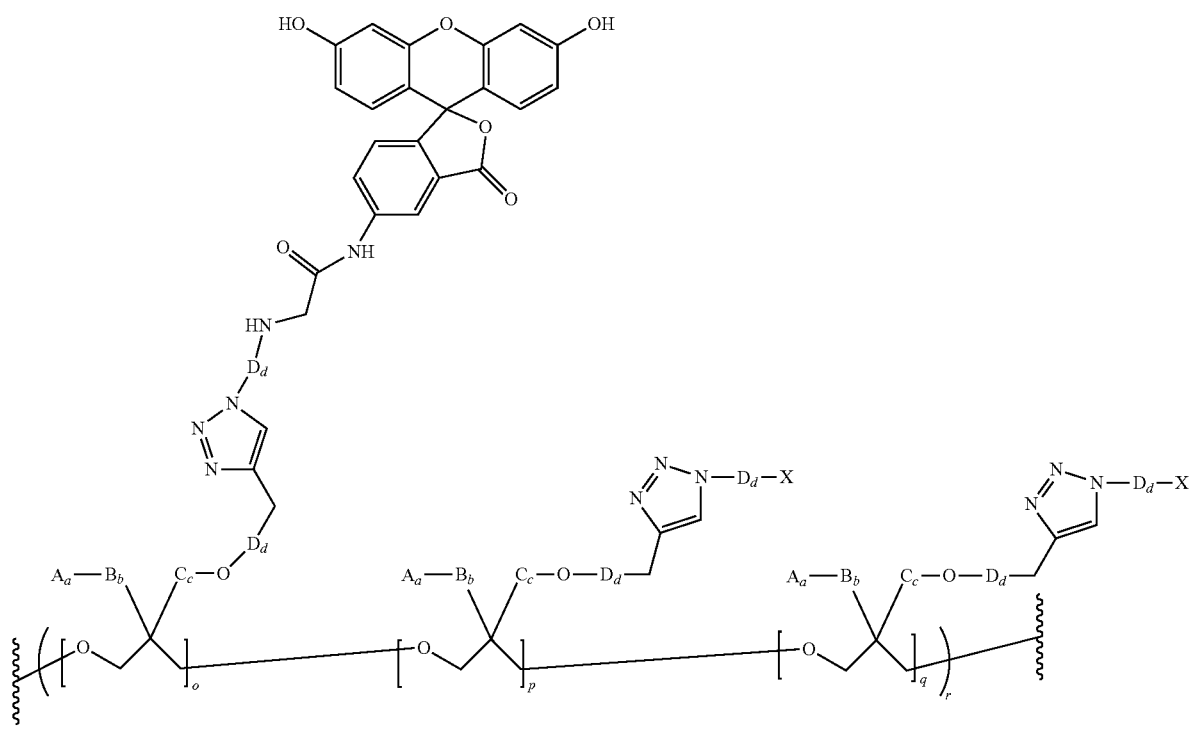

wherein A, B, C, D, a, b, c, d, o, p, q, r, and X are as defined above.

In one embodiment of the foregoing method, the reaction may be suitably carried out using EDC/NHS/NaHCO$_3$, and the like.

In one embodiment of the foregoing method, the first polymer has the formula:

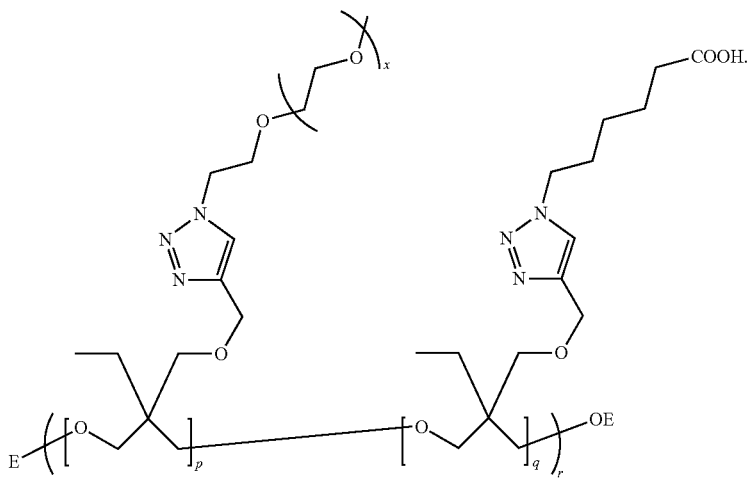

In one embodiment of the foregoing method, the second polymer comprises a subunit having the formula:

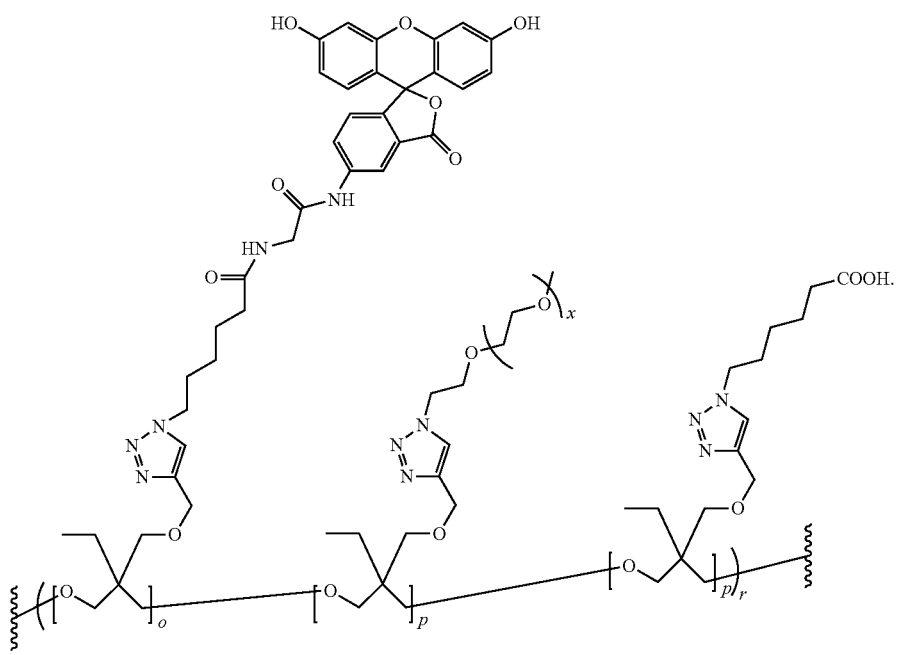

In one embodiment of the foregoing method, the second polymer has the formula:

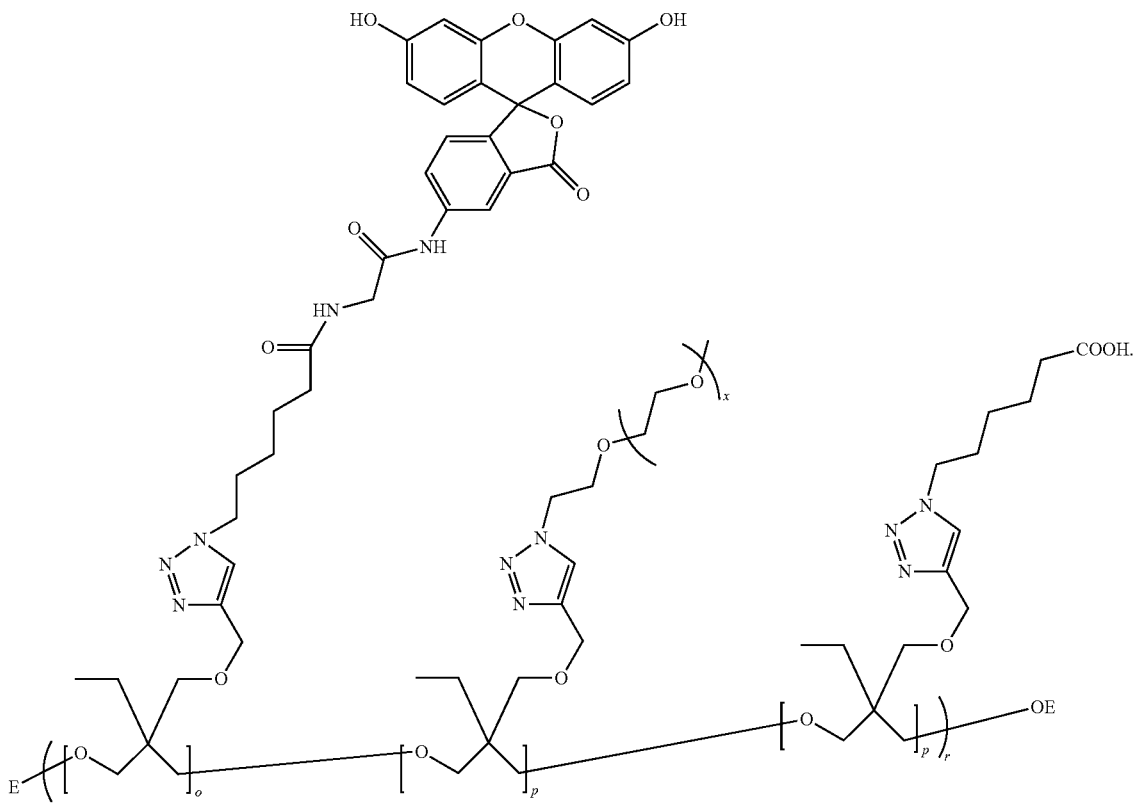
One embodiment provides a method for synthesis, comprising a reaction of a first polymer comprising a subunit having the formula:
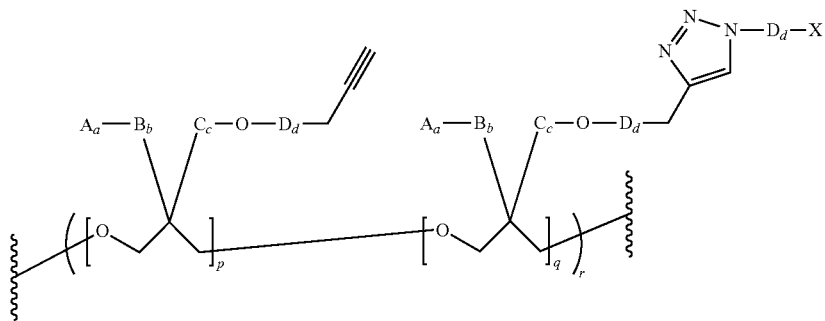
and a compound having the formula:
$$N_3\text{-}D_d\text{-}X \qquad 50$$
to produce a second polymer comprising a subunit having the formula:
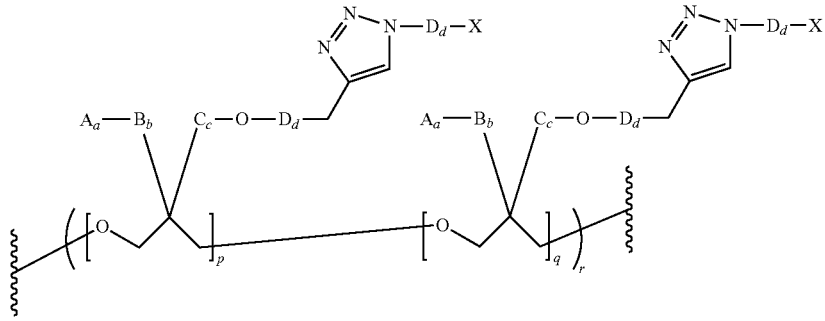

wherein A, B, C, D, a, b, c, d, p, q, r, and X are as defined above.

In one embodiment of the foregoing method, the reaction may be suitably carried out using the "click" reaction, for example, with CuI/PMDTA/THF, CuBr/bi-Py/DMSO, and the like.

In one embodiment of the foregoing method, the first polymer has the formula:

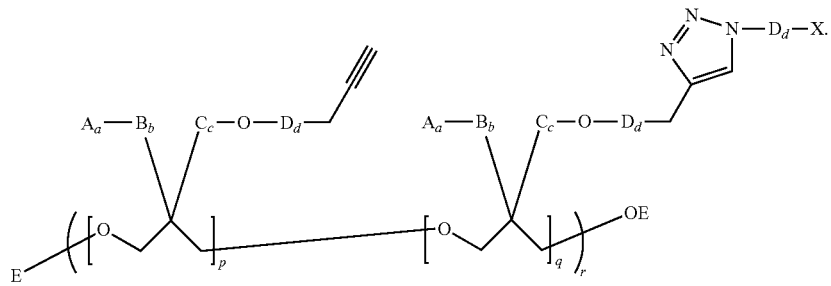

In one embodiment of the foregoing method, the second polymer comprises a subunit having the formula:

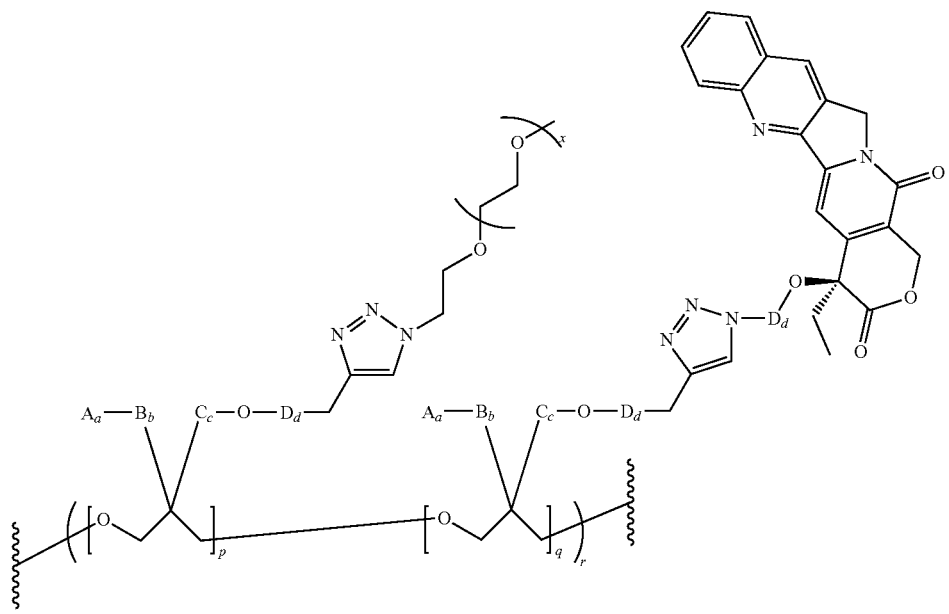

In one embodiment of the foregoing method, the second polymer comprises a subunit having the formula:

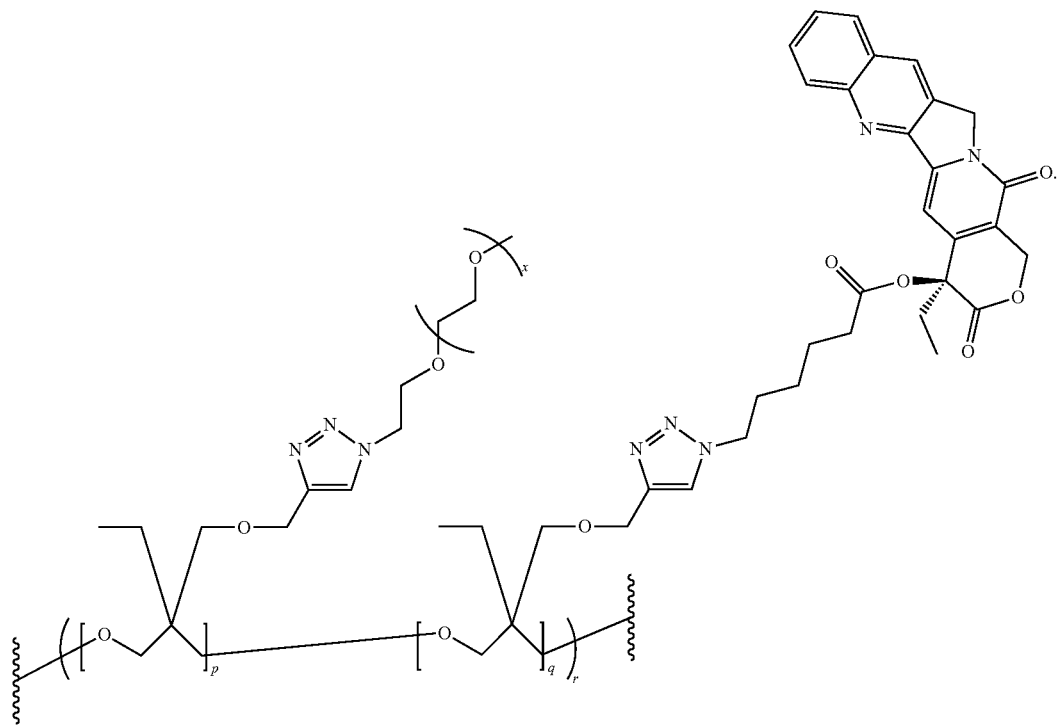
In one embodiment of the foregoing method, the second polymer has the formula:
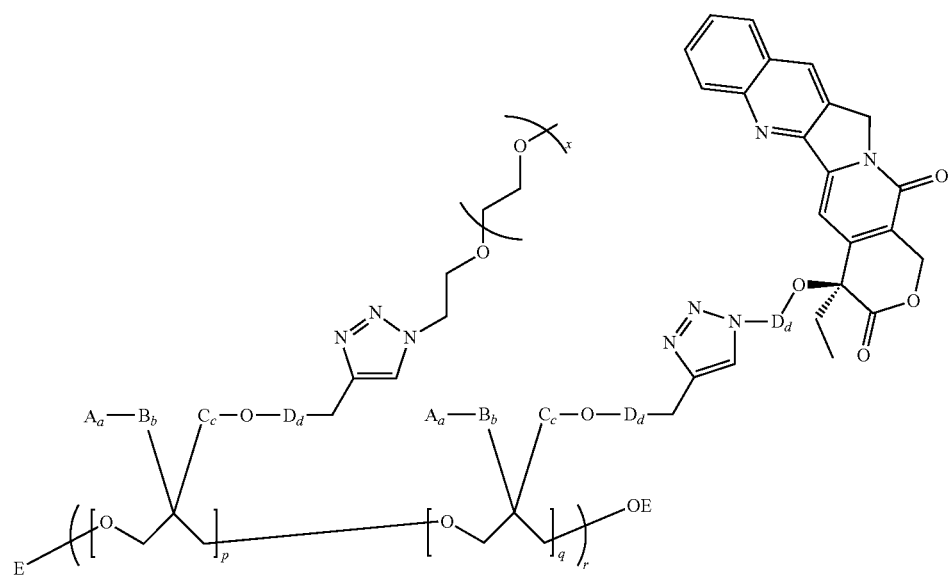
In one embodiment of the foregoing method, the second polymer has the formula:

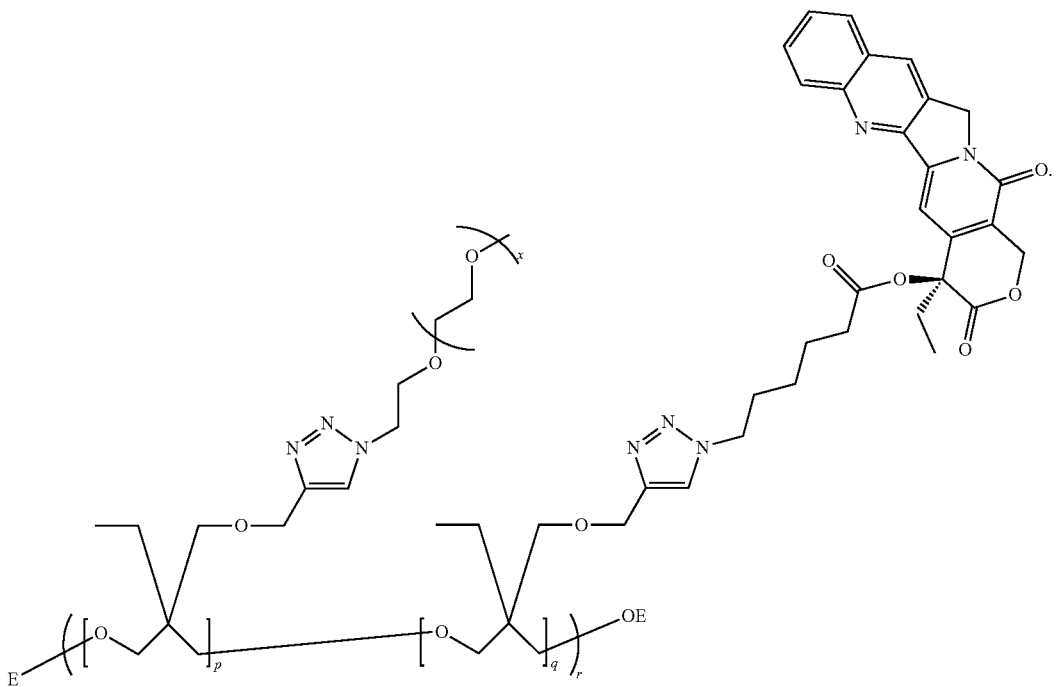

One embodiment provides a synthesis method, comprising a reaction of:

a compound having the formula:

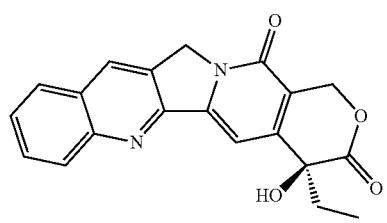 [SMILES: CC[C@@]1(O)C(=O)OCc2c1cc1n(c2=O)Cc2cc3ccccc3nc2-1]

and a compound having the formula:

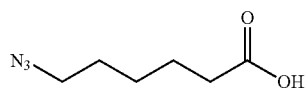 [SMILES: [N-]=[N+]=NCCCCCC(=O)O]

to produce a compound having the formula:

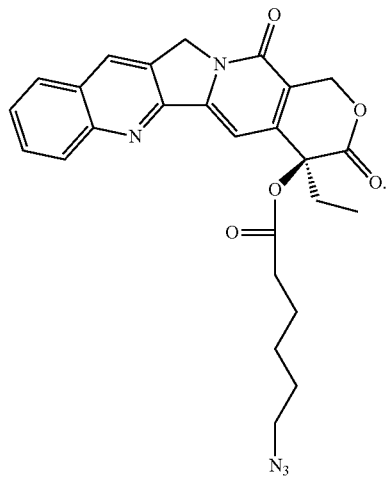 [SMILES: CC[C@@]1(OC(=O)CCCCCN=[N+]=[N-])C(=O)OCc2c1cc1n(c2=O)Cc2cc3ccccc3nc2-1]

In one embodiment of the foregoing method, the reaction may be suitably carried out, for example, EDC/DMAP/DCM and the like.

DETAILED DESCRIPTION OF THE SEVERAL EMBODIMENTS

The inventors have found that the oxetane based polymer carrier with an alkyne pendant group (Poly-Ox-Alkyne or POA herein) in each repeat unit represents an attractive platform for efficient and controlled attachment of a drug or set of drugs, solubilizing groups to improve water solubility and biocompatibility of the macromolecule, a targeting moiety, if desired, that targets the whole system to the targeted cells or disease-related receptors, fluorescence label or other diagnostic agent, if desired, to track the material inside the cells.

The coupling of biological active moieties terminated with azide functional group into polymeric carrier (POA) or its functionalization modification is based on the application of Cu(I)-catalyzed azide-alkyne cycloaddition (CuAAC) or "click" reaction (FIG. 1). The inventors have found that application of CuAAC in the drug delivery systems is compelling and well suited for coupling of biomolecules such as peptides, proteins, and nucleic acids to the synthetic carrier because the reaction uses alkyne and azide functional groups that do not occur naturally. The click reaction is highly selective, gives high yields with few byproducts and can be done with the use of solvent or non-solvent, e.g., water.

Oxetanes can be an essential element in many drugs and play a pivotal role in making drugs to achieve desirable pharmacokinetic properties. Oxetanes can also be utilized as monomers to form linear or branched polymers via ring-opening polymerization (ROP) under different reaction conditions.

In one embodiment, 3-ethyl-3-hydroxymethyl oxetane (EHMO or Ox herein) as monomer can be used to make a promising polymeric drug carrier owing to its bifunctionality. The hydroxyl side groups are readily available for alkylation reaction, while the oxetane ring readily undergoes Lewis acid catalyzed ROP.

Incorporation of alkyne into monomer ensures that every repeat unit of the resulting homopolymer has an alkyne group available for click chemistry, ensuring maximum capacity for drug loading or functionalization.

POA was water insoluble due to the presence of two hydrocarbon pendant groups in the repeat unit. This can limit its utility in biomedical applications, particularly drug delivery. To overcome this limitation, we grafted POA with polyethylene glycol (PEG) via click reaction to make it water soluble and biocompatible. PEG is commonly included in polymer drug delivery systems due to its excellent solubility in water and nontoxicity. Additionally, PEG helps improve pharmacokinetic properties and reduce immunogenicity of polymer-drug bioconjugates.

The present inventors have found that click chemistry provides an efficient, precise means to control post-functionalization of POA through its pendant clickable alkynes.

The inventors have synthesized water soluble cytocompatible polyethylene glycol (PEG)-grafted polyoxetane brush polymers, made through ring-opening polymerization of acetylene-functionalized 3-ethyl 3-hydroxymethyloxetane (EAMO) monomer followed by a click reaction with methoxypolyethylene glycol azide (mPEG-azide). The uniformly distributed alkyne pendant groups make this new platform well suited for delivery of therapeutic and diagnostic agents.

A new family of clickable polyoxetanes has now been found as a modular delivery platform capable of carrying various functional entities such as drugs, imaging agents, and polyethylene glycol (PEG) as a solubility and biocompatibility enhancer.

For the first time, 3-ethyl-3-hydroxymethyl oxetane (EHMO) (FIG. 2) is used as a monomer to make clickable polymeric drug carriers based on bifunctionality. EHMO hydroxyl side group is readily available for alkylation, while the oxetane ring readily undergoes Lewis acid catalyzed ROP. Therefore, EHMO bifunctionality was used to synthesize alkyne-containing polyoxetane P(EAMO) homopolymer as a platform, which allows drug coupling and biofunctionalization via click chemistry. A new synthesis and characterization of a new alkyne-containing polyoxetane P(EAMO) platform. PEG was click grafted to P(EAMO) to generate PEG-grafted brush polymers (P(EAMO)-g-PEGs) with controlled degrees of PEGylation. Cytocompatibility with human dermal fibroblasts was observed and evaluate. Their ability to deliver imaging agents is shown, wherein 5-(aminoacetamido) fluorescein (AAF) was coupled to P(EAMO)-g-PEG via click-able bifunctional spacer 6-azidohexanoic acid. With the aid of AAF, cellular uptake of the fluorescein-labeled brush polymer by human dermal fibroblasts was examined.

EXAMPLES

Example I

A new family of clickable polyethylene glycol (PEG)-grafted polyoxetane brush polymers has been synthesized as a potential modular platform for delivery of drugs and imaging agents. 3-Ethyl-3-hydroxymethyl oxetane (EHMO) monomer reacted with propargyl benzenesulfonate in the presence of sodium hydride to yield alkyne substituted monomer (EAMO). Subsequently, cationic ring opening polymerization using boron trifluoride diethyl etherate (BTDE) catalyst and 1,4-butanediol (BD) initiator produced P(EAMO) homopolymer with a DP of ~30 (30 alkynes per chain). Methoxypolyethylene glycol azide (mPEG750-azide) prepared from mPEG750 (750 gmol$^{-1}$) was grafted to P(EAMO) via copper (I)-catalyzed alkyne-azide cycloaddition (CuAAC) click chemistry. Water soluble cytocompatible P(EAMO)-g-PEG brush polymers with controlled degrees of PEGylation were synthesized by varying the feed molar ratio of mPEG750-azide to alkyne (25:100, 50:100, 75:100, and 100:100). $^1$H NMR, GPC, end group analysis, FTIR, and DSC were applied for polymer characterization. The utility of P(EAMO)-g-PEG for carrying imaging agents was demonstrated by preparing fluorescently labeled P(EAMO)-g-PEG. 5-(Aminoacetamido) fluorescein (AAF) was used as a model compound. Fluorescein-carrying P(EAMO)-g-PEG was synthesized by click coupling bifunctional spacer 6-azidohexanoic acid (AHA) to P(EAMO)-g-PEG and subsequently coupling of AAF to AHA with EDC/NHS chemistry.

Materials. 3-Ethyl 3-hydroxymethyl oxetane (EHMO) was generously provided by Perstorp Polyols (Toledo, Ohio). NaH (60% dispersion in oil), propargyl benzenesulfonate, boron trifluoride diethyl etherate (BF$_3$), 1,4-butanediol (BD), trifluoroacetic anhydride (TFAA), p-toluenesulfonyl chloride, methoxypolyethylene glycol (750 gmol$^{-1}$)(mPEG750), sodium azide (NaN$_3$), copper (I) iodide, N,N,N',N'',N''-pentamethyldiethylenetriamine (PMDTA), copper(II) sulfate pentahydrate, (+)-sodium L-ascorbate, methyl 6-bromohexanoate, lithium hydroxide, N-hydroxysuccinimide (NHS), N-(3-dimethylaminopropyl)-N'-ethylcarbodiimide hydrochloride (EDC), magnesium sulfate (MgSO$_4$), trifluoroacetic anhydride (TFAA), deuterated solvents (CDCl$_3$ and D$_2$O), and other solvents were purchased from Acros (Morris Plains, N.J.). 5-(Aminoacetamido) fluorescein (AAF) was purchased from Invitrogen (Grand Island, N.Y.). SnakeSkin dialysis tubing (cellulose membrane, 3.5K MWCO) was obtained from Thermo Fisher Scientific (Pittsburgh, Pa.). Prior to use, tetrahydrofuran (THF) was distilled over Na in the presence of benzophenone. Dichloromethane (DCM) was washed according to the standard procedure and distilled from CaH$_2$. Silica gel 60 (40-63 µm, 230-400 mesh) was purchased from Sigma-Aldrich (St. Louis, Mo.).

Synthesis of EAMO. EAMO was synthesized as follows: Briefly, sodium hydride NaH (17 g, 0.42 mol) was added portionwise to a solution of EHMO (37 g, 0.32 mol) in 800 ml THF at 5° C. under N$_2$. The suspension obtained was stirred for 1 h at 0° C. before a solution of propargyl benzenesulfonate (95 g, 0.48 mol) in 35 ml of THF was added dropwise. The reaction mixture was stirred at ambient temperature for 2 d followed by cooling to 5° C., pouring into 200 ml of 5 wt % $K_2CO_3$ and stifling for 5 h. Upon removal of THF by rotary evaporation, the product was extracted with DCM, washed with brine, and dried over $MgSO_4$. DCM was then removed under reduced pressure, and the product was distilled at 60-66° C. (1.8 mm Hg) to obtain EAMO. EAMO was further purified by silica gel column chromatography using a hexane/ethyl acetate (7/1: v/v) mixture. Yield 20%.

Synthesis of P(EAMO). $BF_3$ (0.2 g, 1.4 mmol) was added to a solution of BD (72 mg, 0.8 mmol) in 3 ml of DCM, the mixture was stirred for 40 min at room temperature and then cooled 0° C. EAMO (2.5 g, 16 mmol) in 2 ml of DCM was added to the solution at a rate of 0.03 ml/min. After stifling for 12 h at 0° C. under $N_2$, the reaction was quenched with 3 ml of water, and the DCM fraction was collected. The aqueous fraction was extracted again with DCM. The two DCM fractions were combined and dried with $MgSO_4$. DCM was removed under reduced pressure and the residue was precipitated from hexane to obtain P(EAMO) as a viscous liquid.

Synthesis of P(EAMO)-g-PEG Brush Polymers. P(EAMO) was click grafted with mPEG750-azide to make brush polymers. Briefly, a solution containing P(EAMO) (0.65 mmol alkyne equivalent) in 15 ml of THF was prepared and mPEG750-azide addition was adjusted to achieve the following molar feed ratios of mPEG750-azide to alkyne: 25/100, 50/100, 75/100, and 100/100. CuI (12 mg, 0.065 mmol) was added to the solution followed by addition of PMDTA (112 mg, 0.65 mmol). The reaction mixture was stirred under $N_2$ overnight at room temperature. Upon removal of THF by rotary evaporation, the remaining residue was dialyzed against water and then freeze-dried to obtain brush polymers B-#, where # indicates percentage of alkynes per polymer coupled to PEG. According to $^1H$ NMR analysis, brush polymers B-25, 49, 72 and 100% were obtained.

Synthesis of Fluorescein-Carrying Brush Polymers. To use AAF to label the polymer, carboxylate groups were introduced to P(EAMO) using click chemistry. To this end, 6-azidohexanoic acid (AHA), a bifunctional molecule containing a terminal azide and a carboxyl group, was synthesized following a reported method. with modifications and click coupled to the polymer to serve as a spacer for AAF. For instance, AAF-labeled brush polymer on the basis of B-72% was synthesized as follows. Briefly, $CuSO_4$ (8.0 mg, 0.05 mmol) and sodium ascorbate (19.8 mg, 0.1 mmol) were added to a solution of B-72% (100 mg, 4.7 μmol) and AHA (30 mg, 0.2 mmol) in $THF/H_2O$ (2:1, v/v). The mixture was stirred for 24 h at room temperature under $N_2$. Upon removal of THF by rotary evaporation, the remaining residue was dialyzed against water and then freeze-dried to obtain AHA-modified B-72%.

To a solution of AHA-modified B-72% (0.6 μmol) in a mixture of $DMF/H_2O$ (1 ml/0.4 ml), NHS (460 μg, 4 μmol) was added followed by addition of EDC (764 μg, 44 μmol). Following overnight reaction at room temperature, the solvents were removed by rotary evaporation. The obtained NHS ester was dissolved in 4 ml of 0.1 M $NaHCO_3$, to which AAF (3.6 μmol) was added. The reaction mixture was stirred overnight in dark at room temperature, followed by dialysis in water and freeze-drying. To further remove unreacted AAF, the product was dissolved in chloroform and filtered through 5 μm filter. The filtrate was evaporated under reduced pressure to obtain semi-solid product (i.e., AAF-labeled B-72%). The product was kept in dark prior to use. AAF density in the labeled polymer was determined by fluorometry.

End Group Analysis. End group analysis was conducted to determine number-average molecular weight ($M_n$) of P(EAMO). Briefly, excess TFAA was added to a solution of P(EAMO) in $CDCl_3$ and stirred for 30 min at 40° C. $M_n$ was then calculated from the ratio of proton integrals for the shifted methylene protons next to the trifluoroacetyl end groups (α for P(EAMO) and β for butanediol) against methyl proton integral.

Cell Cytotoxicity Assay. Cytotoxicity of P(EAMO)-g-PEG brush polymers was examined using human dermal fibroblasts. The cells were seeded in 24-well plates ($5\times10^3$ cells/well) in 1 ml of growth medium (DMEM medium containing 10% fetal bovine serum (FBS), 100 UI/ml penicillin-streptomycin) at 37° C. in an atmosphere of 10% $CO_2$. After 24 h incubation, the growth medium was replaced with 1 ml of fresh culture medium containing different concentrations of polymer (i.e., 2, 1, 0.5, or 0.25 mg/ml). At 48 h, cell viability was determined using the Trypan blue dye exclusion assay (n=3) (not shown).

Intracellular Uptake Studies. Fibroblasts were seeded on borosilicate glass cover slips in 12-well plates at a density of $5\times10^3$ cells/well and allowed to grow for 24 h in 1 ml of growth medium supplemented with 10% FBS. The cells were incubated for various lengths of time (3, 6, and 24 h) with 100 μg of AAF-labeled B-72% in 1 ml of fresh growth medium supplemented with 10% FBS, fixed with ice-cold methanol for 10 min, counterstained with 4',6-diamidino-2-phenylindole (DAPI), and then rinsed with PBS buffer. True-color fluorescent images (not shown) of the transfected cells were taken under a Zeiss Axiovert 200 inverted fluorescence microscope (Carl Zeiss Microimaging, Inc., Thornwood, N.Y.).

Statistical Analysis. Data were analyzed by analysis of variance (ANOVA), followed by Tukey's test for pairwise comparison of subgroups. P values<0.05 were considered statistically significant.

Results and Discussion Example I

Figure 2:
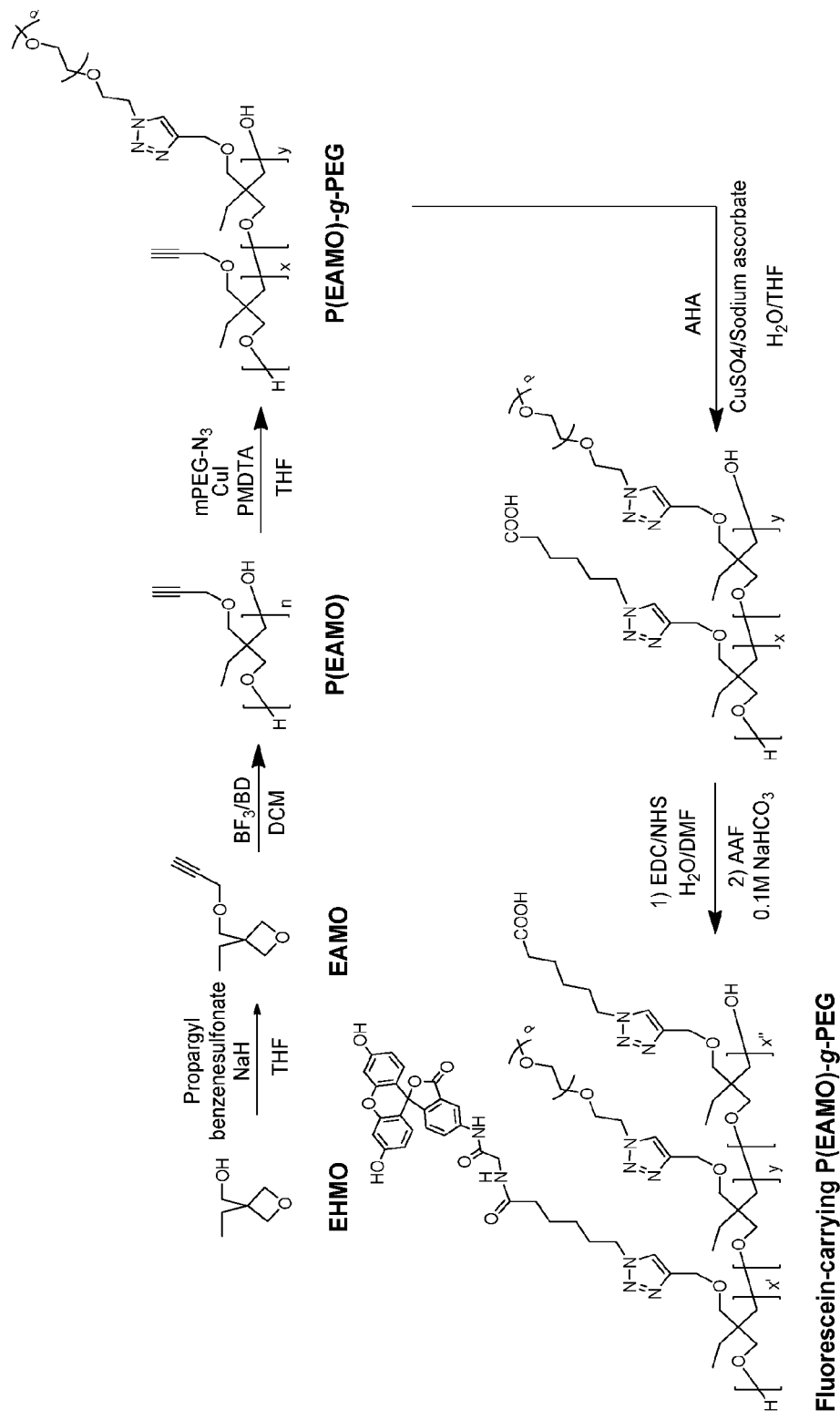
FIG. 2: One embodiment of synthesis of clickable PEG-grafted polyoxetane brush polymers and fluorescein-carrying brush polymer.

Synthesis of P(EAMO). Incorporation of alkyne into monomer ensures that every repeat unit of the resulting homopolymer has an alkyne group available for click reaction, offering an efficient way for drug loading and functionalization. As shown in FIG. 2, alkyne-containing EAMO was synthesized from EHMO and propargyl benzenesulfonate in the presence of NaH and then polymerized via cationic ROP to yield P(EAMO).

$^1H$ NMR spectra (not shown) of acetylene-functionalized monomer EAMO and P(EAMO) indicates successful incorporation of alkyne group into the monomer EHMO as well as preservation of an intact cyclic structure for the monomer.

Synthesis of P(EAMO) was carried out using $BF_3$ catalyst and BD initiator. The reaction was completed within 12 h with high conversion, typically ~95%. Following ring-opening of oxetane, $^1H$ NMR confirmed that all EAMO monomer participated in polymerization, and that alkyne group remained intact during the polymerization.

The presence of alkyne groups in P(EAMO) was also confirmed by FTIR spectroscopy (not shown). $M_n$ of P(EAMO) was determined by GPC (shown) and end group analysis. $M_n$ determined by these two methods were typical of ROP of polyoxetanes: 6500 gmol$^{-1}$ (PDI=2.5) by GPC and 4600 gmol$^{-1}$ by end group analysis. From $M_n$ by end group analysis, P(EAMO) DP was 30. This DP was used for mass balance calculations in subsequent functionalization reactions, as GPC is an indirect determination based on polystyrene standards.

PEG-Grafted Brush Polymers. P(EAMO) is water insoluble due to the presence of two hydrocarbon pendant groups. PEG is commonly included in polymer drug delivery systems due to nontoxicity and good water solubility. Additionally, PEG helps improve pharmacokinetic properties and reduces immunogenicity of polymer-drug bioconjugates. Grafting with mPEG750-azide via click chemistry endowed water solubility and cytocompatibility upon the polymer. Initially, EHMO was PEGylated with mPEG750, but a subsequent ROP was unsuccessful as PEG chain apparently blocked polymer chain growth. Therefore, the "grafting to" method described herein was employed to mitigate steric hindrance. Moreover, the utilization of click chemistry in post-functionalization allows a good control over degree of PEGylation and provides an efficient and controlled way to incorporate drug or other functional entities into the polymer.

P(EAMO) was click grafted with mPEG750-azide at various feed molar ratios of mPEG750-azide to alkyne (25:100, 50:100, 75:100, and 100:100) using the CuI/PMDTA catalytic system. A successful click reaction between alkyne and azide leads to the formation of a triazole linkage. mPEG750-azide was successfully click grafted to P(EAMO). Degree of PEGylation was determined by $^1$H NMR spectra (not shown).

Participation of all alkyne groups in click reaction with mPEG750-azide in B-100% was confirmed. As summarized in Table 1, the degrees of PEGylation determined by $^1$H NMR were close to the feed molar ratios. These results show that click chemistry surprisingly provides an efficient, precise means to control post-functionalization of the P(EAMO) through its pendant clickable alkynes.

GPC results of P(EAMO), B-100%, and mPEG750 are shown in Table 1 and reveal an increase in molecular weight of brush polymers as PEGylation increased. However, the GPC result underestimated molecular weights as compared to the molecular weights determined by $^1$H NMR spectra. The reason of this disagreement might be due to smaller hydrodynamic volumes of brush polymers compared to those of linear polymer standards used in calibration.

TABLE 1

Characterization of P(EAMO) and P(EAMO)-g-PEG brush polymers.

| Polymer Designation | Feed Molar Ratio of mPEG-Azide to Alkyne | Degree of PEGylation (%)[b] | $M_n$ (KDa) | $M_n$[c] (KDa) | PDI[c] |
|---|---|---|---|---|---|
| P(EAMO) | — | 0 | 4.6[a] | 6.5 | 2.5 |
| B-25% | 25:100 | 25 | 10.4[b] | 9.9 | 2.3 |
| B-49% | 50:100 | 49 | 16.0[b] | 10.1 | 1.6 |
| B-72% | 75:100 | 72 | 21.4[b] | 12.3 | 2.4 |
| B-100% | 100:100 | 100 | 27.9[b] | 14.5 | 1.7 |

[a]Determined by end group analysis, DP = 30.
[b]Determined by $^1$H NMR after click chemistry with assumption that no chain broke.
[c]Determined by GPC.

In addition, PEGylation of P(EAMO) via click chemistry was supported by FTIR spectra. The intensities of the alkyne absorption peaks decline with increasing degree of PEGylation. Those peaks were prominent in the spectra of B-25% and B-49%; however, the alkyne absorption peaks were not detected in the spectrum of B-100%, indicating complete substitution of alkynes with mPEG750-azide (spectra not shown). All the resulting copolymers B-25-100% were water soluble. Solubility increased with a higher degree of PEGylation. Grafted copolymers with low degrees of PEGylation might be desirable for drug delivery as more pendant alkynes can be preserved for conjugation with drug or other functional moieties via high efficient click reaction. The solubility of brush polymers with low degrees of PEGylation would be improved by utilization of longer PEG chains for grafting.

Thermal Properties. DSC thermograms for P(EAMO) and P(EAMO)-g-PEG brush polymers were obtained, and transition temperatures and melting enthalpies are listed in Table 2. P(EAMO) is a transparent viscous liquid at room temperature with a $T_g$ of −36.5° C. B-25% displays a lower $T_g$ (−48.7° C.) along with a $T_c$ (−6.6° C.) and a $T_m$ (20.5° C.) attributed to PEG side chain crystallization. $T_g$ values for B-49, 72 and 100% were clearly observed only on the first heating from −53° C. to −60° C. and were not detected from the second heating cycle. The crystallization temperature ($T_c$) of those materials increases in the order of B-49%, B-72% B-100% and correspond to −9.8° C., −5.4° C., and 5.8° C. $T_m$ values for B-25-100%, mPEG750, and mPEG750-azide are in the range of 20-30° C. The melting enthalpies ($\Delta H_m$) increase substantially with increasing PEGylation, emphasizing the association of melting/crystallization with PEG chains.

TABLE 2

Thermal properties of P(EAMO), brush polymers, mPEG750, and mPEG750-azide:

| Polymer Designation | $T_g$ (° C.) | $T_c$ (° C.) | $T_m$ (° C.) | $\Delta H_m$ (J/g) |
|---|---|---|---|---|
| P(EAMO) | −36.5[a] | — | — | — |
| B-25% | −48.7[a] | −6.6 | 20.5 | 28.1 |
| B-49% | −53.6[b] | −9.8 | 24.5 | 61.8 |
| B-72% | −60.6[b] | −5.4 | 22.6 | 67.2 |
| B-100% | −52.6[b] | 5.8 | 30.0 | 75.6 |
| mPEG750 | −78.0[a] | 15.0[c] | 27.5 | — |
| mPEG750-azide | −64.0[a] | 17.0[d] | 27.0 | — |

[a]From the 2$^{nd}$ heating cycle.
[b]From the 1$^{st}$ heating cycle.
[c]A small crystallization peak found at 17° C.
[d]A small crystallization peak found at 20° C. .

Fluorescein-Carrying Brush Polymers. Imaging agents have become an integral component of a delivery system for real-time tracking, disease detection or diagnosis. To demonstrate the ability of P(EAMO)-g-PEG brush polymers to carry imaging agents, we explored a method to endow the synthesized brush polymers with AAF, which is a water soluble fluorescent marker. AAF has an amine group available for coupling chemistry. AHA—a bifunctional spacer carrying a carboxyl group and an azide group was coupled to B-72% via click reaction between the remaining alkyne groups and azide of AHA. Carboxyl groups introduced to the polymer through AHA were then used for coupling of AAF using EDC/NHS chemistry.

It is noteworthy that click reaction between AHA and B-72% using the CuI/PMDTA catalytic system did not succeed. Instead, an alternate CuSO$_4$/sodium ascorbate catalyst/ligand system successfully triggered the click reaction, generating AHA-modified B-72%. $^1$H NMR spectra (not shown) suggests that all the remaining alkynes were click coupled with AHA and supports conjugation of AHA to the polymer. The carboxyl groups introduced to the polymer through AHA were activated by EDC/NHS chemistry and then coupled with AAF. An average of 1.3 AAF molecules per polymer was determined by fluorometry.

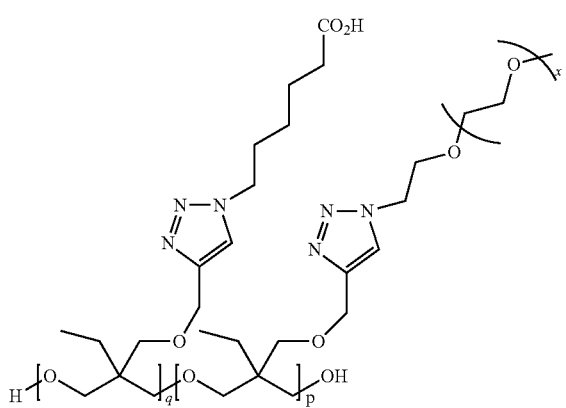

Figure 3:
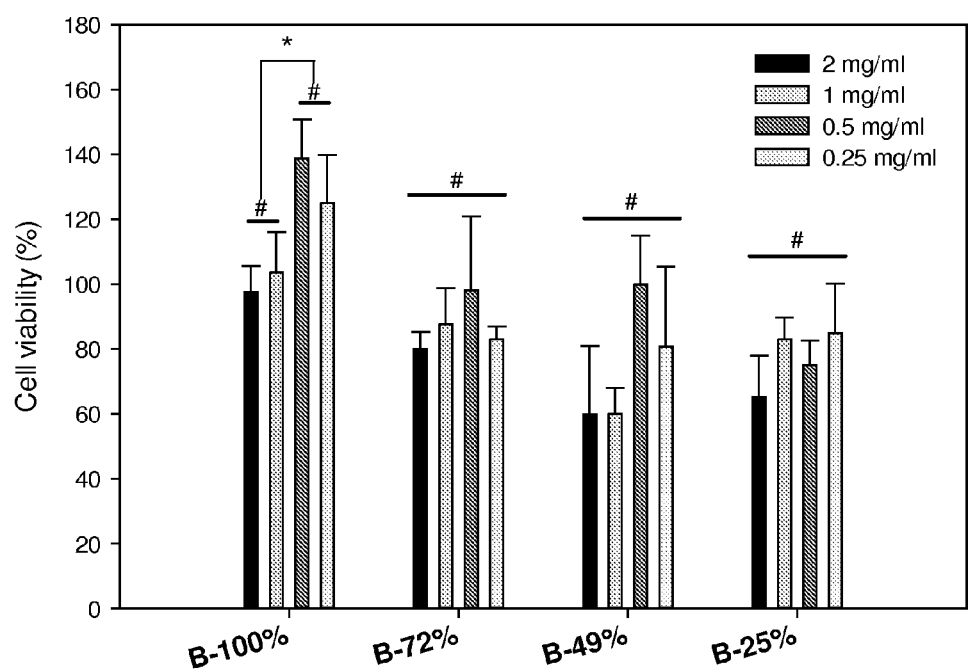
FIG. 3: Cytotoxicity of P(EAMO)-g-PEG brush polymers to human dermal fibroblasts according to the trypan blue assay. Cell viability was determined by normalizing the number of viable cells in each group to that of viable cells in the control (untreated) (# denotes no significant difference between subgroups, *denotes p<0.05).

Cytotoxicity and Cellular Uptake. Toxicity of P(EAMO) was not evaluated because it is insoluble in water. PEG chains were essential for enhancing P(EAMO) water solubility and cytocompatibility. The cytotoxicity of the synthesized P(EAMO)-g-PEG brush polymers B-25-100% to human dermal fibroblasts was studied. In general, toxicity of polymers is dose-dependent. According to the trypan blue results presented in FIG. 3, B-100% did not reduce cell viability at tested concentrations from 0.25 to 2 mg/ml. B-72%, B-49%, and B-25% with less degrees of PEGylation caused a slight decrease in viability of fibroblasts. Our statistical analysis shows that an increase in PEGylated polymers concentration from 0.25 mg/ml to 2 mg/ml did not cause cell viability to decrease, implying that the cells tolerated a relatively broad range of polymer concentrations. Furthermore, cross-group comparisons of viability of the cells treated with B-72%, B-49%, and B-25% showed that all the treated cells invariably maintained a high viability (~80%), suggesting that those PEGylated copolymers were equally cytocompatible. Within the range of degree of PEGylation investigated, less PEGylated copolymers may be preferable drug carriers as they tend to reserve more alkynes for click reactions with drug or other functional moieties. Fibroblasts were commonly used for general toxicity assessment of polymers.

AAF-labeled B-72% was used as a model to examine polyoxetane cellular uptake. At the tested polymer concentration, the treated cells were 100% viable. Cellular uptake results (not shown) show that AAF-labeled B-72% was taken up quickly by the cell and evenly distributed predominately in the cytoplasm at 3 h. It was also found in the nucleus according to colocalization of DAPI-stained nuclei. At 6 h and 24 h an increase in fluorescence intensity indicated more polymer was taken up into the cytoplasm. More AAF-labeled B-72% entered the nucleus as incubation time was extended.

Results and Discussion Example I

P(EAMO) homopolymer is a new, clickable polyoxetane, from which a family of PEGylated polyoxetane brush polymers has been synthesized. MPEG750-azide was synthesized and click coupled to the polymer to yield brush polymers. While P(EAMO) is insoluble, all PEG-grafted P(EAMO) brush polymers are water soluble and compatible with human dermal fibroblasts at concentrations up to 2 mg/ml. This new family of clickable polymer is particularly suited for delivery of drugs or other functional entities of interest via a highly efficient click reaction.

Example II

Water soluble camptothecin (CPT)-polyoxetane conjugates were synthesized using a clickable polymeric platform P(EAMO) that was made by polymerization of acetylene-functionalized 3-ethyl-3-hydroxymethyl oxetane (i.e., EAMO). CPT was first modified with a linker 6-azidohexanoic acid via an ester linkage to yield CPT-azide. CPT-azide was then click coupled to P(EAMO) in dichloromethane using bromotris(triphenylphosphine) copper(I)/N,N-diisopropylethylamine. For water solubility and cytocompatibility improvement, methoxypolyethylene glycol azide (mPEG-azide) was synthesized from mPEG 750 gmol$^{-1}$ and click grafted using copper(II) sulfate and sodium ascorbate to P(EAMO)-g-CPT. $^1$H NMR spectroscopy confirmed synthesis of all intermediates and the final product P(EAMO)-g-CPT/PEG. CPT was found to retain its therapeutically active lactone form. The resulting P(EAMO)-g-CPT/PEG conjugates were water soluble and produced dose-dependent cytotoxicity to human glioma cells and increased γ-H2AX foci formation, indicating extensive cell cycle-dependent DNA damage. Altogether, the present inventors have synthesized CPT-polymer conjugates able to induce controlled toxicity to human cancer cells.

Materials. Bromotris(triphenylphosphine) copper(I) CuBr (PPh$_3$)$_3$, N,N-diisopropylethylamine (DIPEA), 4-dimethylaminopyridine (DMAP), N-(3-dimethylaminopropyl)-N'-ethylcarbodiimide hydrochloride (EDC), copper(II) sulfate (CuSO$_4$), (+)-sodium L-ascorbate, magnesium sulfate MgSO$_4$, deuterated solvents, dichloromethane (DCM), and other solvents were purchased from Acros (Morris Plains, N.J.). 20(S)-Camptothecin (95%) (CPT) and silica gel 60 (40-63 μm, 230-400 mesh) were purchased from Sigma-Aldrich (St. Louis, Mo.). Cy5.5 azide was purchased from Lumiprobe (Hallandale Beach, Fla.). 6-Azidohexanoic acid (AHA) was synthesized by us following a reported method with slight modifications. Methoxypolyethylene glycol azide (mPEG-azide) was synthesized from mPEG 750 gmol$^{-1}$. Dialysis tubing, snake skin MWCO 3500, was obtained from Thermo Fisher Scientific (Pittsburgh, Pa.).

Figure 4:
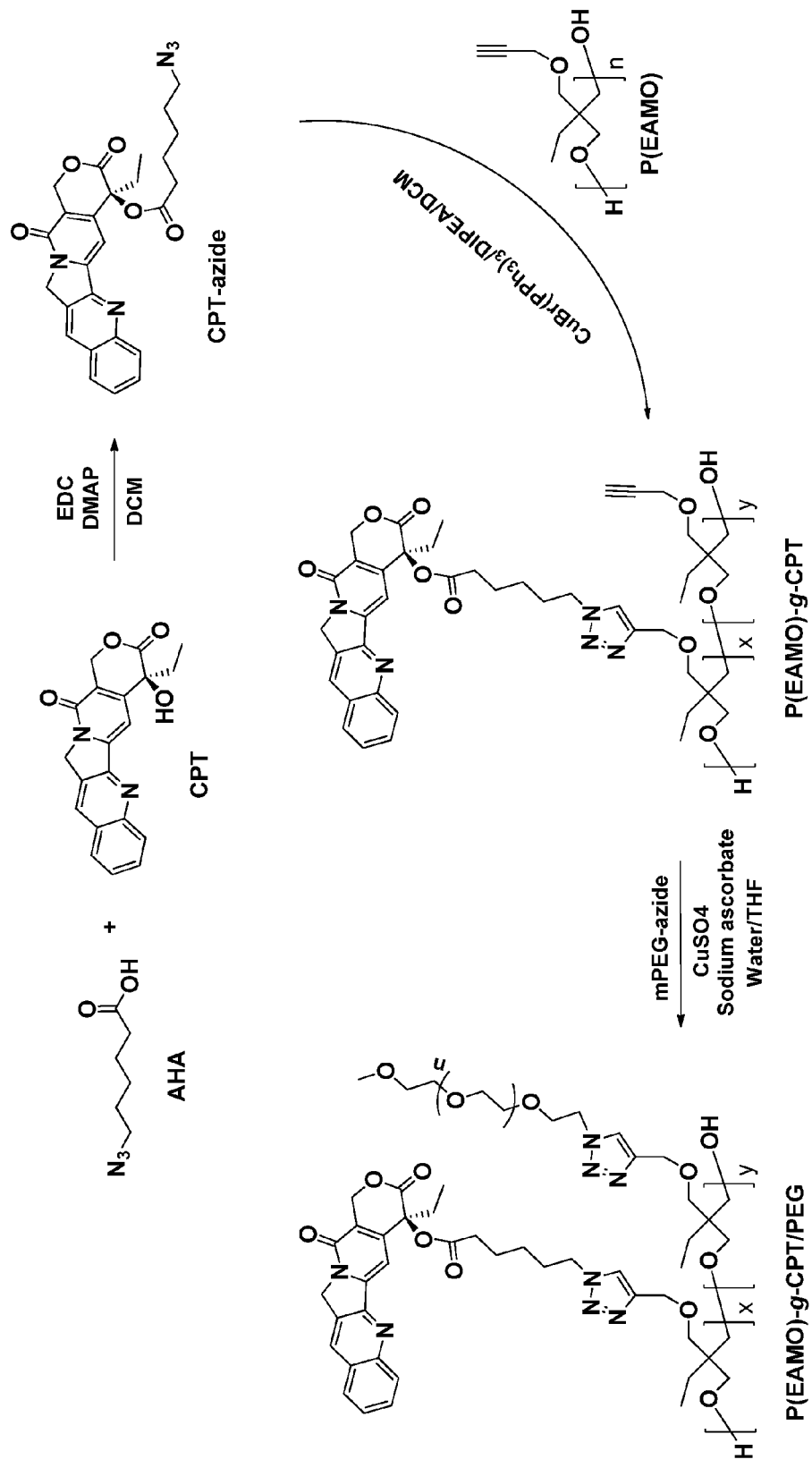
FIG. 4: One embodiment of synthesis scheme of P(EAMO)-g-CPT/PEG conjugates via CuAAC click chemistry.

Synthesis of Azide-Functionalized Camptothecin (CPT-Azide). Azide was introduced to CPT via a hydrophobic spacer AHA. CPT (190 mg, 0.55 mmol), AHA (170 mg, 1.1 mmol), DMAP (66 mg, 0.55 mmol), and EDC (0.2 g, 1.1 mmol) were dissolved in 50 ml of DCM and stirred for 36 h (FIG. 4). Afterwards, the reaction solution was poured into water and extracted with DCM. The combined organic fractions were dried over MgSO$_4$. Upon removal of DCM by rotary evaporation, the remaining residue was purified by column chromatography on silica gel using DCM/methanol (90/2.5: v/v). Yield: 60%.

Synthesis of P(EAMO)-g-CPT conjugates. Ring-opening polymerization of acetylene-functionalized 3-ethyl 3-hydroxymethyloxetane (EAMO) to make P(EAMO) (M$_n$=4640 gmol$^{-1}$, PDI=2.45) was carried out. P(EAMO) (32 mg, 0.2 mmol acetylene equivalent) and CPT-N$_3$ (25 mg, 0.05 mmol) were dissolved in 3 ml of DCM. To the solution DIPEA (0.2 ml, 1 mmol) was added followed by addition of CuBr(PPh$_3$)$_3$ (9.6 mg, 0.01 mmol). The reaction mixture was heated at reflux with stifling for 24 h under nitrogen and then dialyzed against DCM for 48 h. After DCM was removed by rotary evaporation, P(EAMO)-g-CPT conjugates were precipitated in cold ether, filtered, and dried. Yield: 51%.

Synthesis of P(EAMO)-g-CPT/PEG conjugates. P(EAMO)-g-CPT (10 mg, 27 µmol acetylene equivalent) and mPEG-azide (25 mg, 32 µmol) were dissolved in a mixture of THF/water (3/1: v/v). CuSO$_4$ (8 mg, 32 µmol) and sodium ascorbate (12 mg, 60 µmol) were added to the solution. The reaction mixture was stirred at 70° C. under N$_2$ for 24 h. Upon removal THF by rotary evaporation, the remaining solution was dialyzed against water for 20 h and freeze-dried to obtain P(EAMO)-g-CPT/PEG conjugates. Yield: 81%. According to $^1$H NMR spectroscopy, the remaining alkynes reacted completely with mPEG-azide. That is to say, the resulting P(EAMO)-g-CPT/PEG conjugates had an average of 22.5 PEG chains per polymer.

In addition, P(EAMO)-g-PEG without CPT attachment was also synthesized with the same degree of PEGylation as P(EAMO)-g-CPT/PEG. A portion of P(EAMO)-g-PEG was further labeled with Cy5.5 azide. The click reaction was performed in a mixture of DMSO/water (1/1: v/v) using the same conditions as above. The obtained polymer was purified on Sephadex G-50 using chloroform as eluent. An average of 1 Cy-5.5 molecule was attached to the polymer chain according to fluorometry.

Cell toxicity assays. Human glioma U1242/luc-GFP cells stably expressing the reporter luciferase were exposed to various CPT equivalent concentrations of polymer-CPT conjugates or polymer control samples (n=4) in a 96-well microtiter plate for 48 h followed by luciferase assay to assess survival of cells. Repair foci formation was carried out using anti-γ-H2AX antibody (Upstate/Millipore, MA) and secondary anti-mouse-Alexa Fluor-488 antibody (Molecular Probes-Invitrogen). Cells were imaged using a Zeiss LSM 710 Meta imaging system and analyzed using PerkinElmer's Volocity software.

Results and Discussion Example II

The inventors have developed a new family of water soluble cytocompatible PEG-grafted polyoxetane brush polymers via ring-opening polymerization of acetylene-functionalized 3-ethyl-3-hydroxymethyl oxetane (EAMO) and subsequent click coupling of P(EAMO) with mPEG azide. The presence of alkyne group in each repeat unit resulted in a polymeric backbone with a high density of alkyne groups (DP=30) available for drug coupling or attachment of solubilizing side chains and/or other biologically active molecules using CuAAC click chemistry. Due to the high efficiency of click chemistry, PEG grafting density in P(EAMO)-g-PEG can be precisely controlled by changing the feed molar ratio of mPEG-azide to alkyne of P(EAMO). Importantly, P(EAMO)-g-PEG brush polymers with a wide range of PEG grafting density are water soluble and cytocompatible.

Since the lactone ring of CPT is responsible for drug binding to TOP I enzyme, it is critical to maintain CPT in the lactone form during coupling reactions. Acylation of the hydroxyl group of CPT has been commonly employed based on the observation that modifications at this site do not change the structure of the lactone ring. As shown in FIG. 4, CPT was acylated with a bifunctional hydrophobic spacer AHA carrying both azide and carboxyl groups using EDC/DMPA coupling reaction. In this reaction, CPT was coupled to AHA via an ester linkage. The reaction was performed in DCM at room temperature. The resulting CPT-azide was purified using silica gel column chromatography. $^1$H NMR spectrum of CPT-azide:

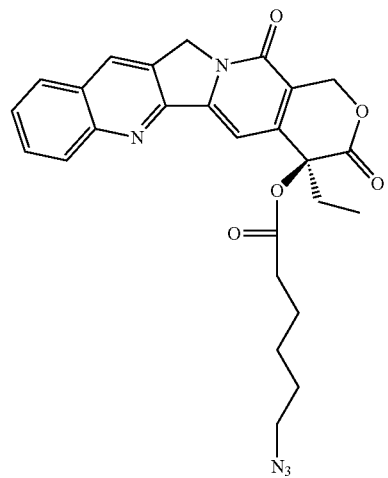 [SMILES: CC[C@@]1(OC(=O)CCCCCN=[N+]=[N-])C(=O)OCc2c1cc1n(c2=O)Cc2cc3ccccc3nc2-1]

confirms that the lactone ring remained intact.

The choice of reaction conditions for click coupling CPT-azide is important since it can result in structural change of the drug and loss of activity. A general catalyst/ligand/solvent reaction condition for CuAAC click chemistry is CuI/alkyl amine/DMF. However, such a condition results in transformation of CPT into the corresponding hydroxy derivative in the presence of oxygen. To avoid this problem, CPT-azide was click grafted to P(EAMO) using CuBr(PPh$_3$)$_3$/DIPEA/DCM. CuBr/2,2-bipyridine/DMSO click reaction condition was also found to be efficient in click coupling CPT-azide to P(EAMO).

$^1$H-NMR spectrum of the resultant P(EAMO)-g-CPT

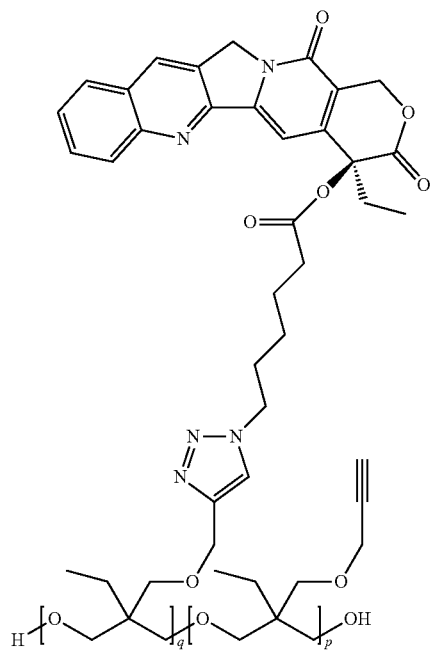

confirms click coupling of CPT to P(EAMO) and indicates the success of the click reaction. $^1$H-NMR spectrum show that all the proton chemical shifts of CPT in the drug-polymer conjugates were identical to those of CPT-azide, indicating that no structural change of CPT occurred during the click reaction was observed. The presence of unreacted alkynes was indicated by ¹H-NMR spectrum (not shown). The ratio of proton integral of methylene (d) adjacent to the triazole linkage resulting from the CPT coupling to that of methylene (d') adjacent to the unreacted alkyne revealed that an average of 7.5 CPT molecules were coupled to the polymer.

The P(EAMO)-g-CPT conjugates are water insoluble. To make them water soluble, P(EAMO)-g-CPT conjugates were further grafted with mPEG-azide via click chemistry catalyzed by CuSO₄ in the presence of sodium ascorbate. ¹H-NMR spectrum of the compound

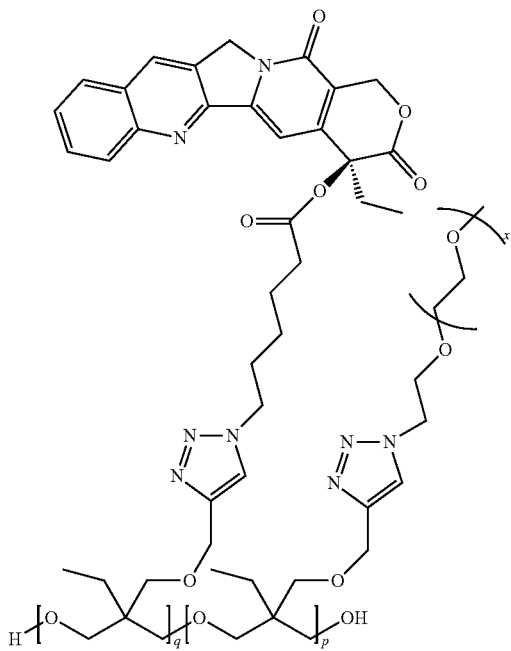

confirmed the incorporation of PEG and complete substitution of remaining alkynes. Importantly, the resulting P(EAMO)-g-CPT/PEG conjugates were water soluble.

Figure 5:
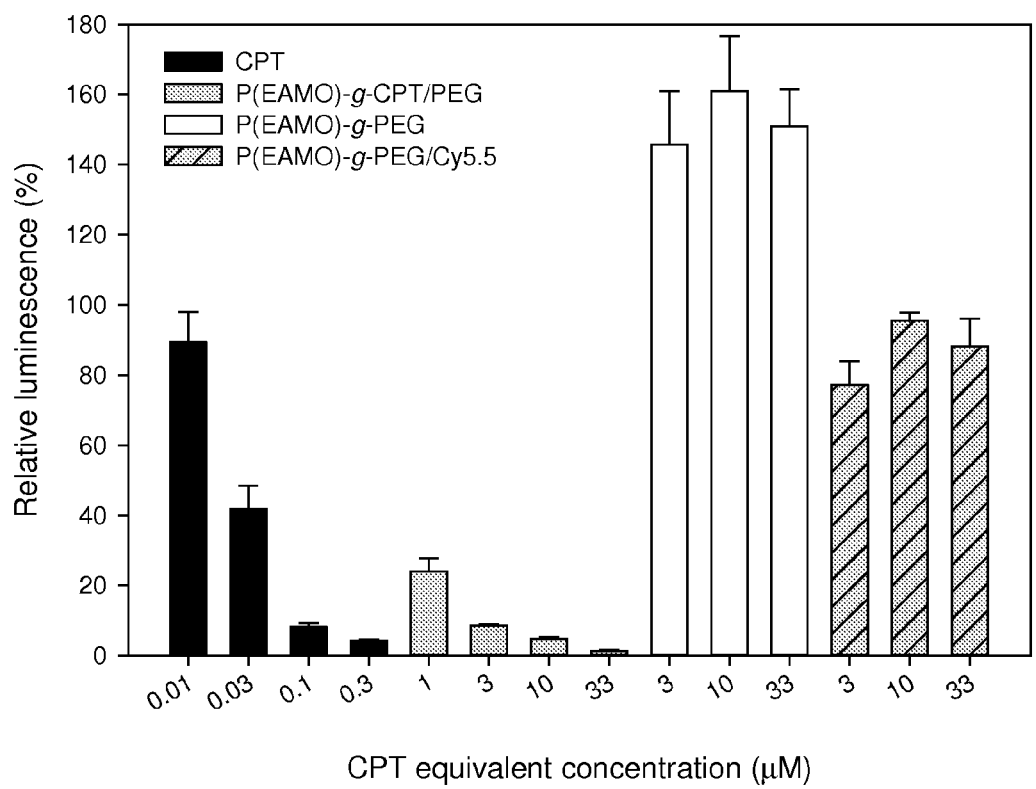
FIG. 5: In vitro cytotoxicity evaluation by luciferase assay.

P(EAMO)-g-CPT/PEG and control groups including free CPT, P(EAMO)-g-PEG, and P(EAMO)-g-PEG/Cy5.5 were tested on U1242/luc-GFP cells for cytotoxicity by luciferase assay. P(EAMO)-g-PEG and P(EAMO)-g-PEG/Cy5.5 were not toxic at concentrations up to 33 µM. In contrast, P(EAMO)-g-CPT/PEG was found to be dose-dependent toxic, similar to free CPT (FIG. 5). As expected, P(EAMO)-g-CPT/PEG was less potent than free CPT at the same CPT equivalent concentration in causing toxicity, likely due to slow release. Chen et al. reported that the AHA linker connecting CPT to poly(methacryloyloxyethyl phosphorylcholine) was stable in aqueous solutions at different pHs. This observation prompted this group to employ more hydrophilic linkers for CPT coupling to accelerate CPT release. The lowest IC$_{50}$ of their polymer-drug conjugates possessing more hydrophilic linker was 2.3 µM in colon (COLO205) adenocarcinoma cells. P(EAMO)-g-CPT/PEG having AHA linker described above was still potent in glioma cells. Cell viability dropped to 24% following 48 h incubation of 1 µM of P(EAMO)-g-CPT/PEG. Given that toxicity of polymer-drug conjugates is also cell type-dependent, our preliminary work indicated that therapeutic application of P(EAMO)-g-CPT/PEG is promising. Indeed, in some applications, maintaining a stable linkage between the drug and the polymer before polymer-drug conjugates enter the target cell is a desirable strategy to avoid premature drug release. Therefore, P(EAMO)-g-CPT/PEG is presumed to undergo ester linkage hydrolysis following cellular uptake to release CPT to recover its therapeutic activity, hence enabling sustained release and longer activity.

In addition, toxicity-induced repair foci formation in human U1242 glioma cells was examined (spectra not shown). CPT interferes with DNA synthesis and is thus most toxic to cells in S phase. Therefore, DNA damage in the form of double-strand breaks are mostly seen in S/G2 cells which is detected by the accumulation of γ-H2AX foci. These cells treated with P(EAMO)-g-CPT/PEG produced extensive γ-H2AX foci after 24 h indicative of DNA damage. The size of the foci in S-phase is relatively small compared to those formed in G1 by, for example, radiation. An absence of foci was observed in a subset of cells treated with P(EAMO)-g-CPT/PEG, presumably those outside of S. Overall, P(EAMO)-g-CPT/PEG showed antitumor activity that supported release of CPT from the polymer and subsequent selective DNA damage in a subset of cells. Since the composition of CPT and PEG can be precisely modulated, a higher drug payload can be achieved without comprising water solubility of the polymer-drug conjugates.

CPT in the lactone form has now been successfully coupled to PEG-grafted polyoxetane brush polymers via CuAAC click chemistry. These polymer-drug conjugates were water soluble and surprisingly demonstrated potent toxicity to glioma cells, while the carrier itself was not toxic. Because of high efficiency and selectivity of the click chemistry, PEG-grafted polyoxetane brush polymers represent a modular platform for efficient delivery of anticancer drugs and functionalization.

Example III

Below is reaction involved in end group analysis and ¹H NMR spectrum of P(EAMO) after reaction with TFAA:

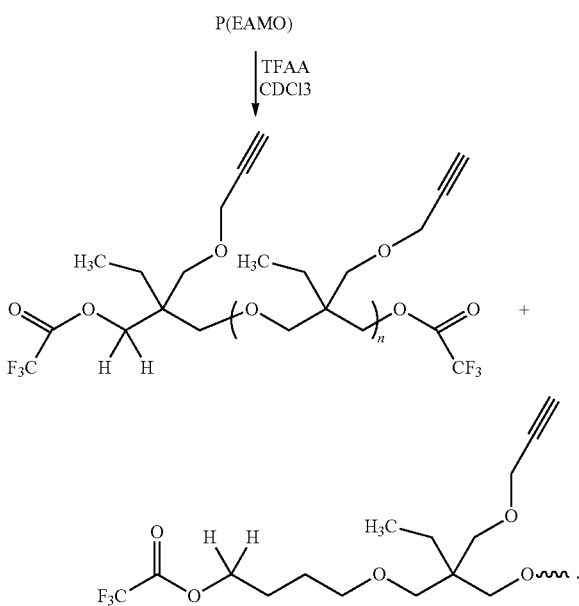

Synthesis of mPEG750-Ts:

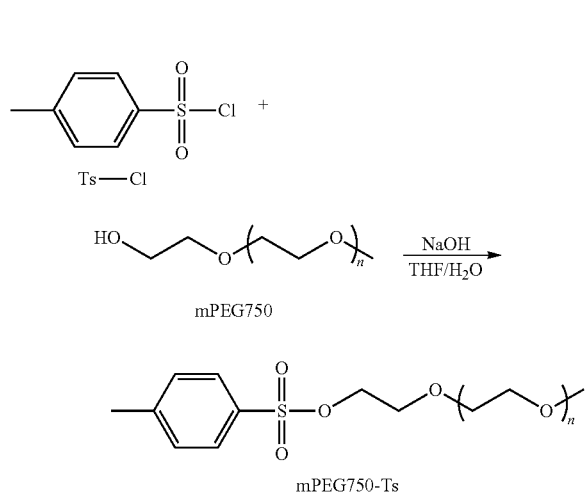

Synthesis of MPEG750-Ts. To mPEG750 (20 g, 26.6 mmol) and NaOH (4.2 g, 106 mmol) in a THF/water mixture (45/8: v/v) p-toluenesulfonyl chloride (8.9 g, 46.6 mmol) in 15 ml of THF was added dropwise at 0° C. The reaction mixture was stirred at 0° C. for 2 h and at room temperature for another 24 h. The layers were separated; aqueous fraction was extracted with DCM. The combined organic fractions were washed with 10% NaOH then with brine and dried over MgSO$_4$. Yield 90%.

Synthesis of mPEG750-azide:

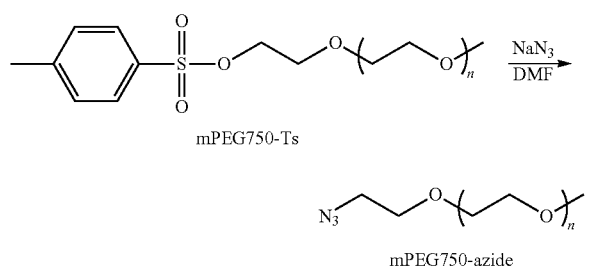

Synthesis of MPEG750-azide. To a solution of mPEG750-Ts (10 g, 11 mmol) in 20 ml of DMF, NaN$_3$ (3.6 g, 55 mmol) was added portionwise. The obtained mixture was stirred for 48 h at 70° C. under N$_2$. After removing DMF via rotary evaporation, the remained residue was diluted with water. The material was extracted with DCM. The combined organic fraction was washed with brine and dried over MgSO4. After DCM was removed by rotary evaporation the crude product was subjected to column chromatography on silica gel using DCM/MeOH (100/8: v/v) as eluent. Yield 65%. GPC: Mn=800 gmol$^{-1}$, PDI=1.10.

Synthesis of Methyl 6-azidohexanoate:

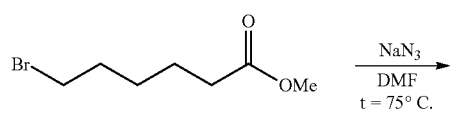

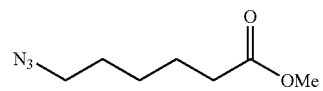

Synthesis of Methyl 6-Azidohexanoate. Methyl 6-azidohexanoate was synthesized via a modified literature procedure. A reaction mixture of methyl 6-bromohexanoate (6 g, 29 mmol) and NaN$_3$ (9.4 g, 144 mmol) in 30 ml of DMF was stirred at 75° C. for 14 h under N$_2$. After cooling down, the reaction mixture was poured into water. The product was extracted with hexane, washed with brine, and dried under MgSO$_4$. Solvent was evaporated to give transparent liquid. Yield: 95%.

Synthesis of AHA:

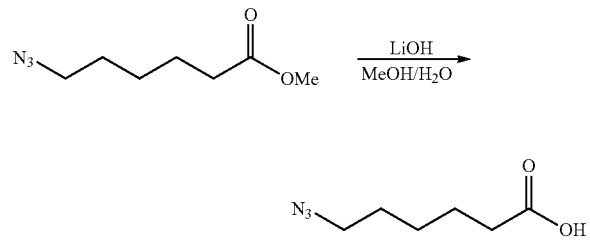

Synthesis of 6-Azidohexanoic Acid (AHA). AHA was synthesized following a reported method with modifications. To methyl 6-azidohexanoate (3.4 g, 20 mmol) in 20 ml of mixture of MeOH/H$_2$O (4/1 v/v) LiOH (2.5 g, 60 mmol) was added. After being stirred for 5 h at room temperature, the reaction mixture was poured into brine and washed with hexane to remove unreacted Ester. The aqueous fraction was acidified with HCl, extracted with ethyl acetate. Combined organic fractions were washed with brine and died over MgSO$_4$. Ethyl acetate was removed under reduced pressure that resulted to transparent liquid. Yield 93%.

The contents of U.S. Provisional Application No. 61/695,927, filed Aug. 31, 2012, are incorporated herein by reference.

The invention claimed is:

1. A polymer, comprising a subunit having the formula:

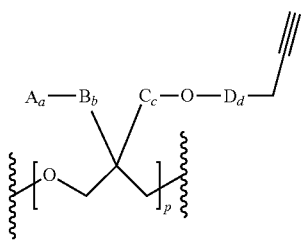

wherein:
A is independently hydrogen, $C_{1-10}$ alkyl, $C_{3-10}$ alkenyl, $C_{3-10}$ alkynyl, $C_{3-20}$ cycloalkyl, $C_{5-20}$ cycloalkenyl, $C_{5-25}$ aryl, —OR$^1$, —COOR$^1$, —C(O)R$^1$, —C(O)-halogen, —SR$^1$, —OSO$_2$R$^1$, —CONR$^1$R$^2$, —NR$^1$R$^2$, —N$_3$, or halogen;

B is independently $C_{1-10}$ alkylene, $C_{3-10}$ alkenylene, $C_{3-10}$ alkynylene, $C_{3-20}$ cycloalkylene, $C_{5-20}$ cycloalkenylene, $C_{5-25}$ arylene, —COO—, —C(O)—, —S—, —CONR$^1$—, —NR$^1$—, —CH$_2$CH$_2$O—, —O—, or combination of two or more of the foregoing;

C is independently $C_{1-10}$ alkylene, $C_{3-10}$ alkenylene, $C_{3-10}$ alkynylene, $C_{3-20}$ cycloalkylene, $C_{5-20}$ cycloalkenylene, $C_{5-25}$ arylene, —COO—, —C(O)—, —S—, —CONR$^1$—, —NR$^1$—, —CH$_2$CH$_2$O—, —O—, or combination of two or more of the foregoing;

D is independently $C_{1-10}$ alkylene, $C_{3-10}$ alkenylene, $C_{3-10}$ alkynylene, $C_{3-20}$ cycloalkylene, $C_{5-20}$ cycloalkenylene, $C_{5-25}$ arylene, —COO—, —C(O)—, —S—, —CONR$^1$—, —NR$^1$—, —CH$_2$CH$_2$O—, —O—, or combination of two or more of the foregoing;

a is 1;
b is independently 0-10;
c is independently 1-20;
d is independently 0-20;
p is greater than 0;
R$^1$ and R$^2$ are independently hydrogen, $C_{1-10}$ alkyl, $C_{3-10}$ alkenyl, $C_{3-10}$ alkynyl, $C_{3-20}$ cycloalkyl, $C_{5-20}$ cycloalkenyl, or $C_{5-25}$ aryl;

and wherein one or more of the alkyl, alkenyl, alkynyl, cycloalkyl, cycloalkenyl, aryl, alkylene, alkenylene, alkynylene, cycloalkylene, cycloalkenylene, and arylene may independently be branched, unbranched, unsubstituted, substituted, or contain at least one heteroatom.

2. The polymer of claim 1, which has the formula:

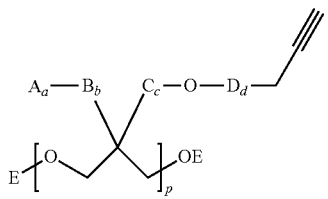

wherein E is hydrogen or —C(O)CH=CH$_2$.

3. The polymer of claim 1, wherein A is —CH$_3$, B is —CH$_2$—, and C is —CH$_2$—; a, b and c are 1; and d is 0.

4. The polymer of claim 2, wherein E is hydrogen.

5. A polymer, comprising a subunit having the formula:

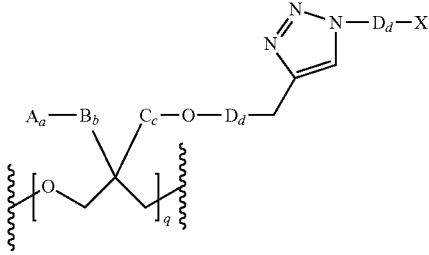

wherein:

A is independently hydrogen, $C_{1-10}$ alkyl, $C_{3-10}$ alkenyl, $C_{3-10}$ alkynyl, $C_{3-20}$ cycloalkyl, $C_{5-20}$ cycloalkenyl, $C_{5-25}$ aryl, —OR$^1$, —COOR$^1$, —C(O)R$^1$, —C(O)-halogen, —SR$^1$, —OSO$_2$R$^1$, —CONR$^1$R$^2$, —NR$^1$R$^2$, —N$_3$, or halogen;

B is independently $C_{1-10}$ alkylene, $C_{3-10}$ alkenylene, $C_{3-10}$ alkynylene, $C_{3-20}$ cycloalkylene, $C_{5-20}$ cycloalkenylene, $C_{5-25}$ arylene, —COO—, —C(O)—, —S—, —CONR$^1$—, —NR$^1$—, —CH$_2$CH$_2$O—, —O—, or combination of two or more of the foregoing;

C is independently $C_{1-10}$ alkylene, $C_{3-10}$ alkenylene, $C_{3-10}$ alkynylene, $C_{3-20}$ cycloalkylene, $C_{5-20}$ cycloalkenylene, $C_{5-25}$ arylene, —COO—, —C(O)—, —S—, —CONR$^1$—, —NR$^1$—, —CH$_2$CH$_2$O—, —O—, or combination of two or more of the foregoing;

D is independently $C_{1-10}$ alkylene, $C_{3-10}$ alkenylene, $C_{3-10}$ alkynylene, $C_{3-20}$ cycloalkylene, $C_{5-20}$ cycloalkenylene, $C_{5-25}$ arylene, —COO—, —C(O)—, —S—, —CONR$^1$—, —NR$^1$—, —CH$_2$CH$_2$O—, —O—, or combination of two or more of the foregoing;

X is A, pharmaceutically active agent, physiological targeting agent, diagnostic agent, peptide, protein, nucleic acid, imaging agent, or combination of two or more of the foregoing;

a is 1;
b is independently 0-10;
c is independently 1-20;
d is independently 0-20;
q is greater than 0;
R$^1$ and R$^2$ are independently hydrogen, $C_{1-10}$ alkyl, $C_{3-10}$ alkenyl, $C_{3-10}$ alkynyl, $C_{3-20}$ cycloalkyl, $C_{5-20}$ cycloalkenyl, or $C_{5-25}$ aryl;

and wherein one or more of the alkyl, alkenyl, alkynyl, cycloalkyl, cycloalkenyl, aryl, alkylene, alkenylene, alkynylene, cycloalkylene, cycloalkenylene, and arylene may independently be branched, unbranched, unsubstituted, substituted, or contain a hetero atom.

6. The polymer of claim 5, which has the formula:

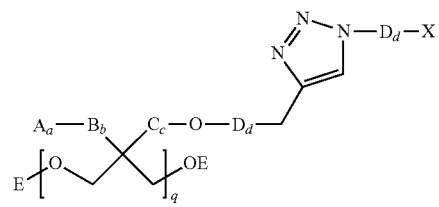

wherein E is hydrogen or —C(O)CH=CH$_2$.

7. The polymer of claim 6, wherein E is hydrogen.

8. The polymer of claim 5, wherein the pharmaceutically active agent is docetaxel, gemcitabine, epirubicin, paclitaxel, geldanamycin, doxorubicin, camptothecin, topotecan, irinotecan, 9-aminocaptothecin, fluorouracil, platinate, cisplatin, carboplatin, DACH-Pt, anti-angiogenic drug, anti-fibrotic agent, CNS-active agent, therapeutic sensitizer, ATM kinase inhibitor, phosphatidylinositol 3-kinase/protein kinase, ATR kinase, DNA-PKcs kinase, cardio-vascular drug, immune-stimulating drug, antimicrobial agent, antiparasitic agent, anti-inflammatory agent, analgesic, anesthetic, or combination of two or more thereof.

9. The polymer of claim 5, wherein the pharmaceutically active agent is camptothecin.

10. The polymer of claim 5, wherein the subunit has one of the following formulas:

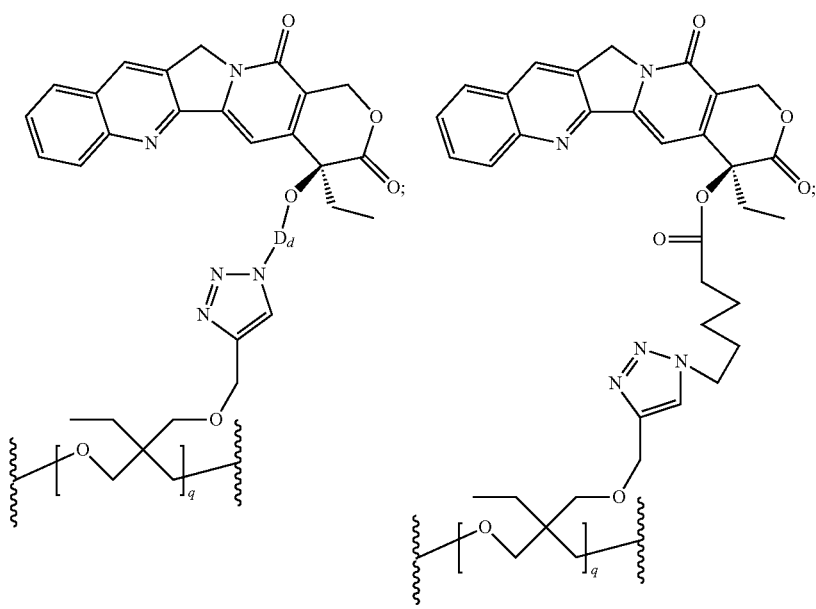
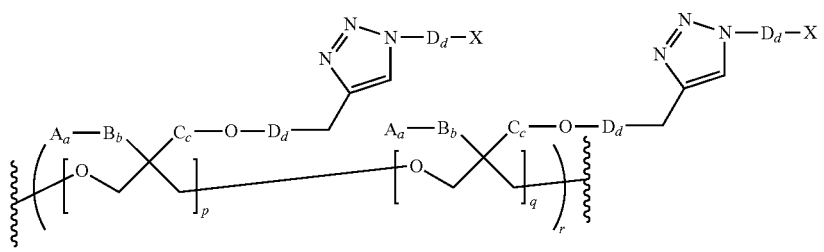
wherein p, q and r are greater than 0;
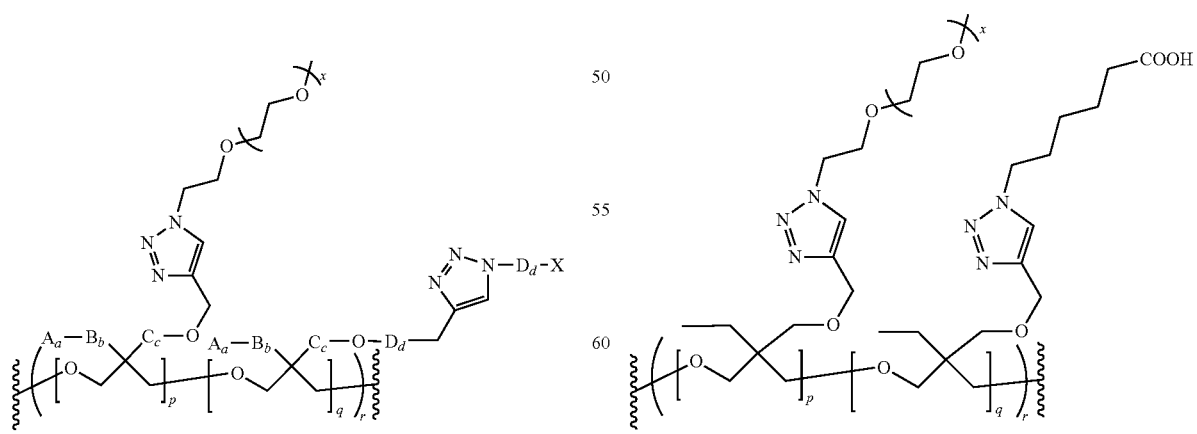
wherein p, q, r and x are greater than 0;
wherein p, q, r and x are greater than 0;

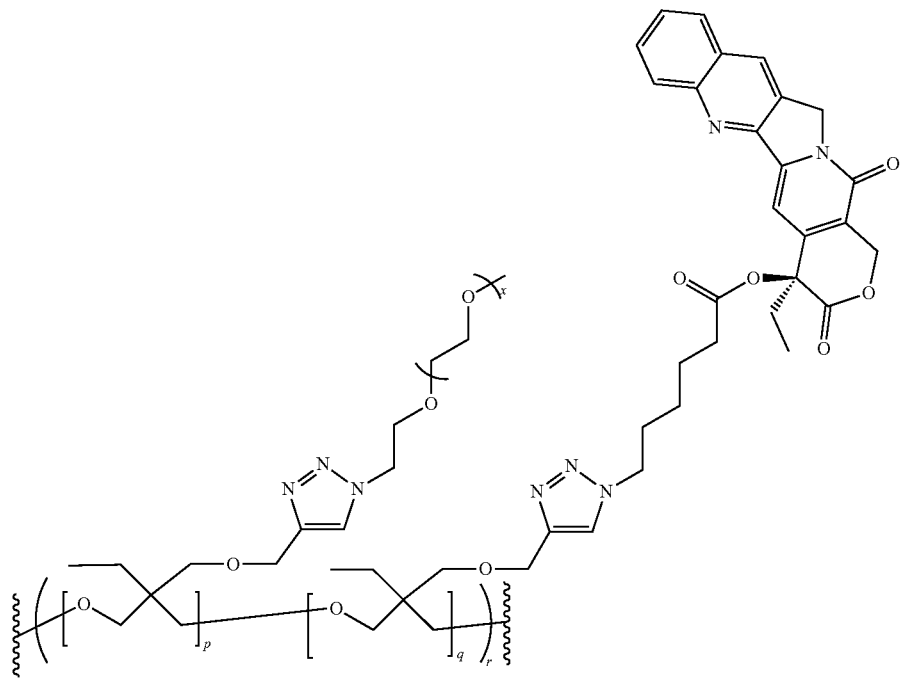
wherein p, q, r and x are greater than 0;
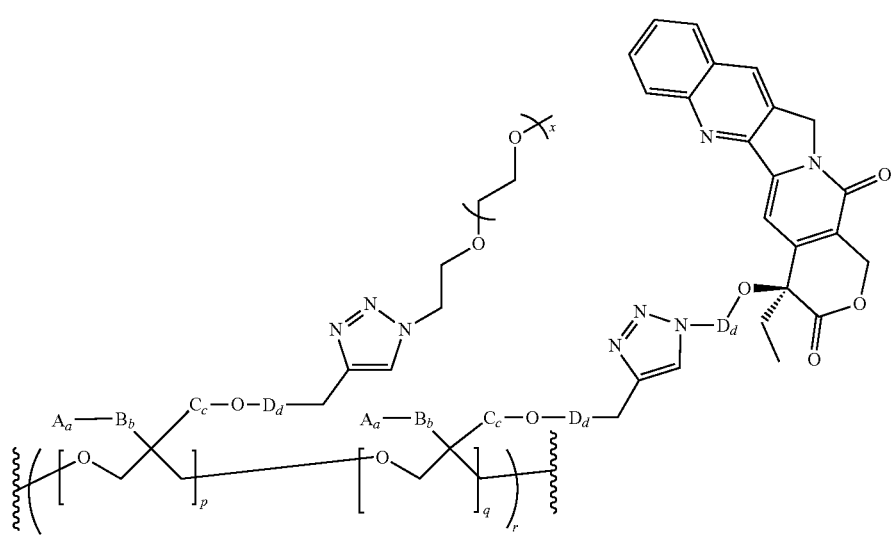
wherein p, q, r and x are greater than 0;

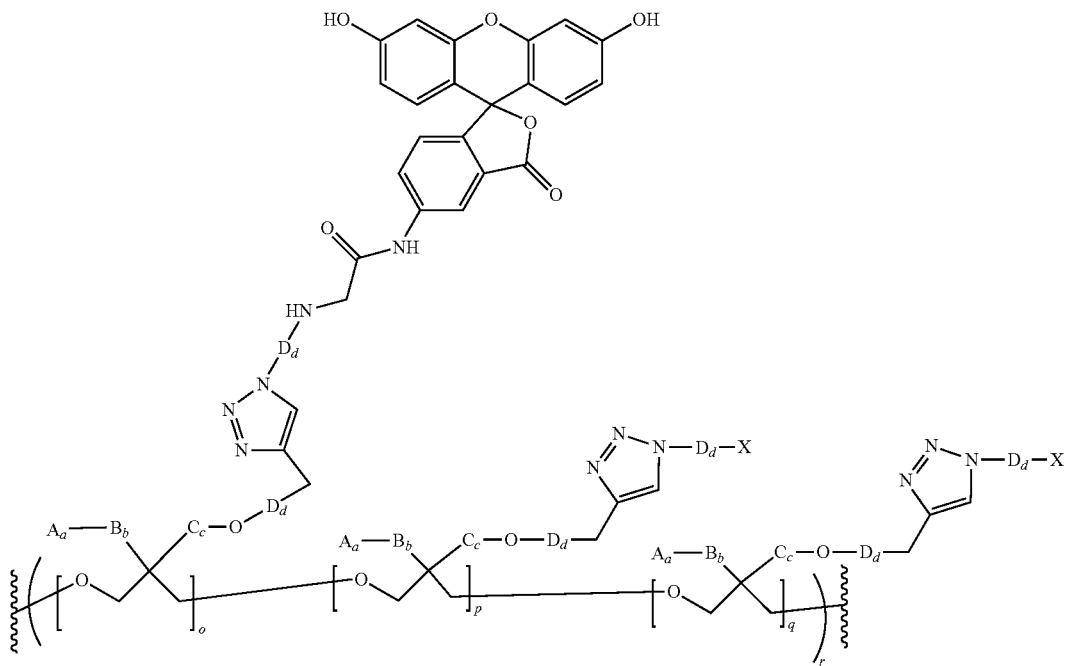
wherein o, p, q, and r are greater than 0;
or
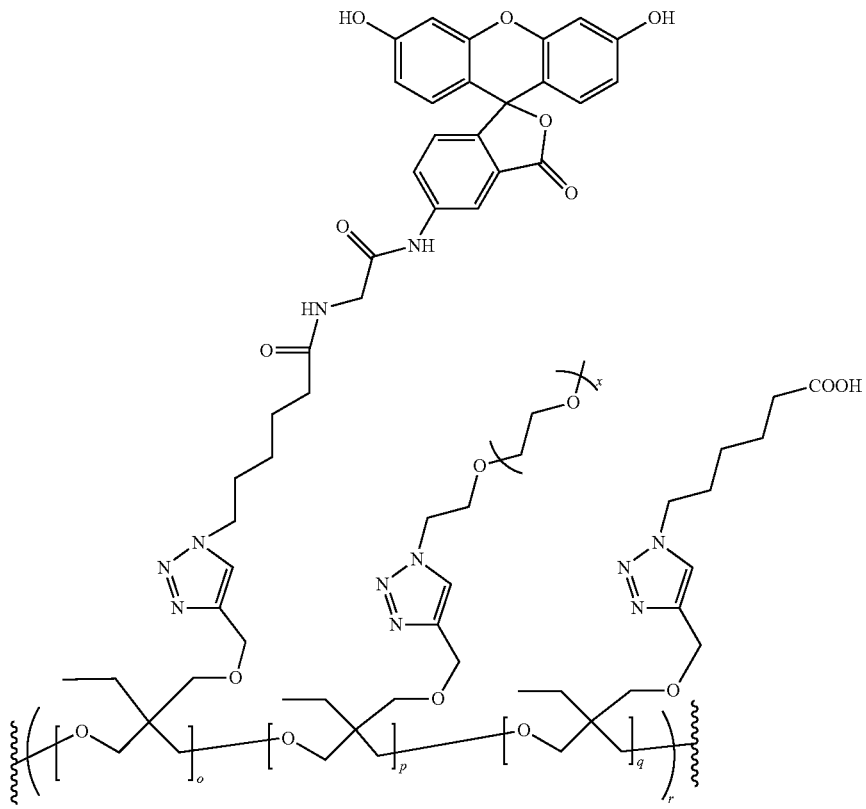
wherein o, p, r and x are greater than 0.
11. The polymer of claim 5, which has one of the following formulas:

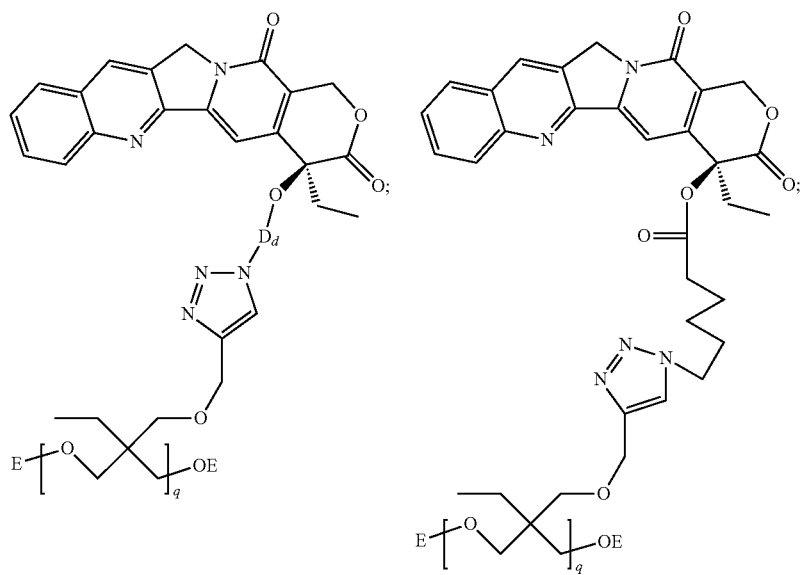
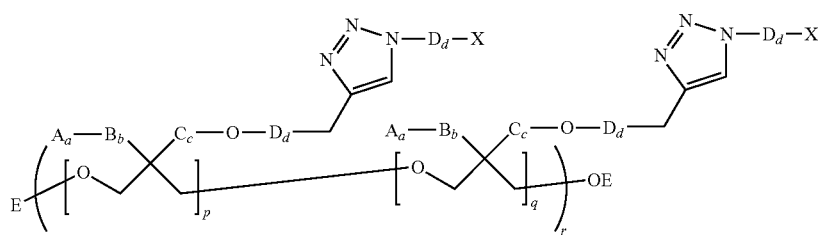
wherein p, q and r are greater than 0;
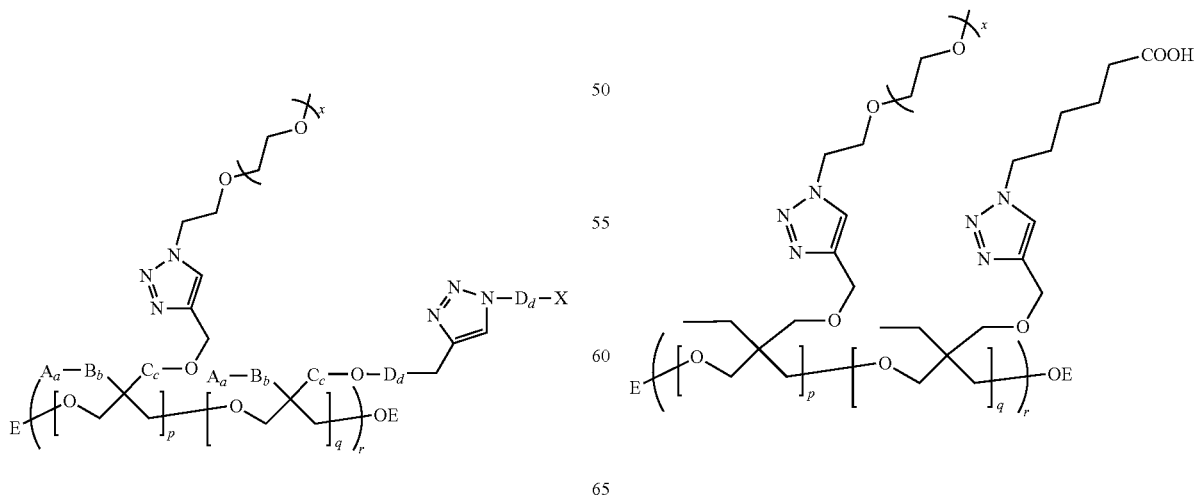
wherein p, q, r and x are greater than 0;
wherein p, q, r and x are greater than 0;

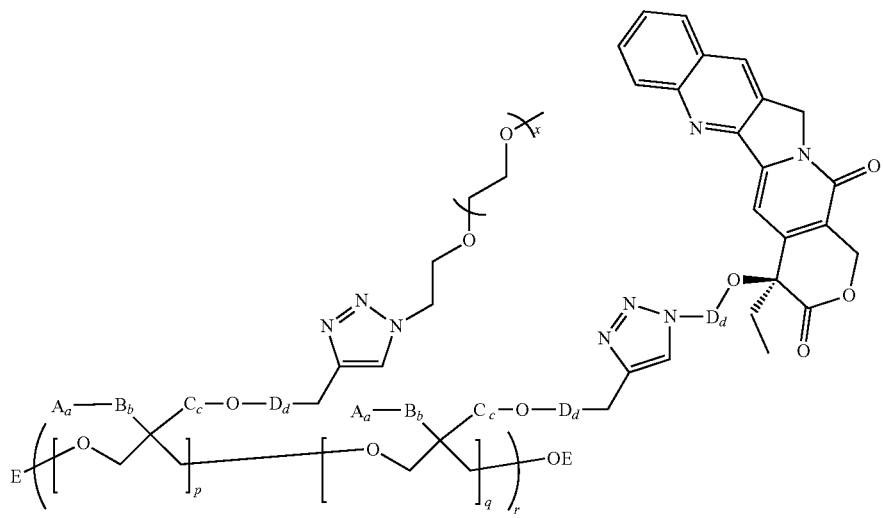
wherein p, q, r and x are greater than 0;
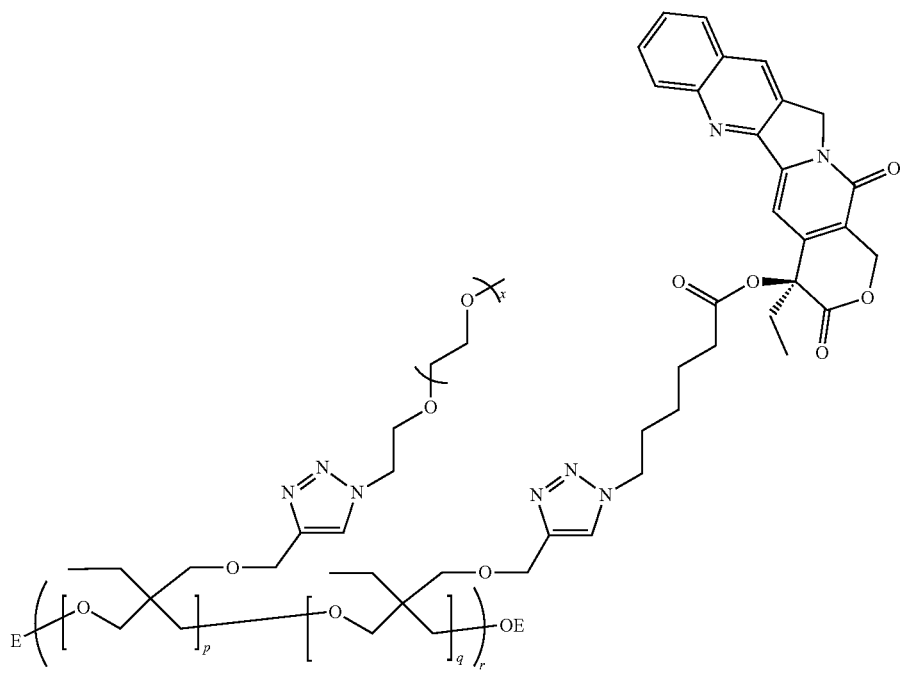
wherein p, q, r and x are greater than 0;

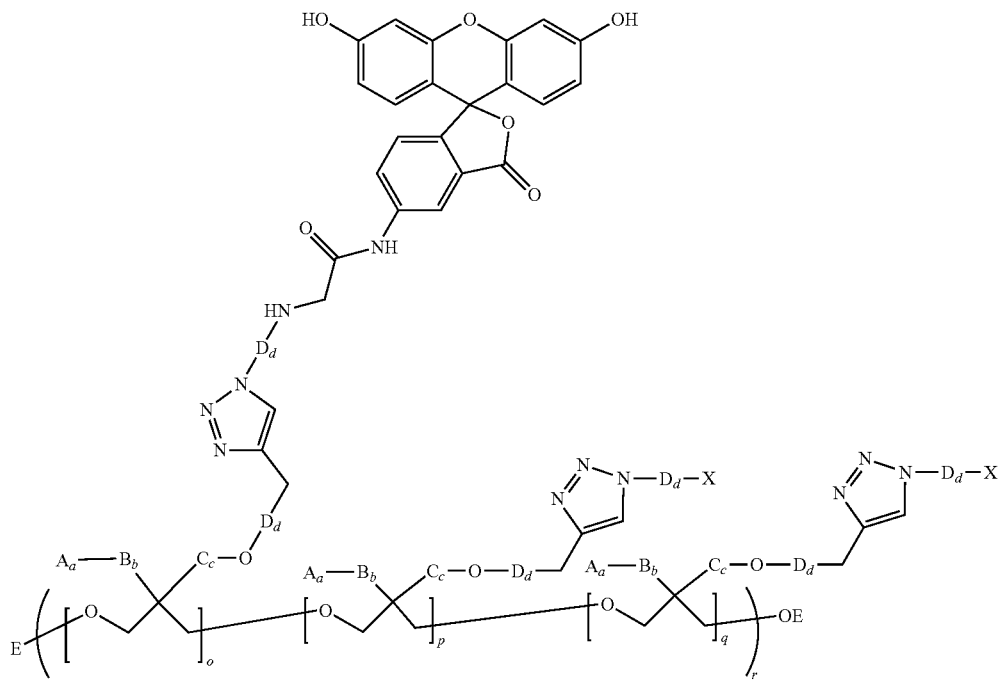
wherein o, p, q, and r are greater than 0;
or
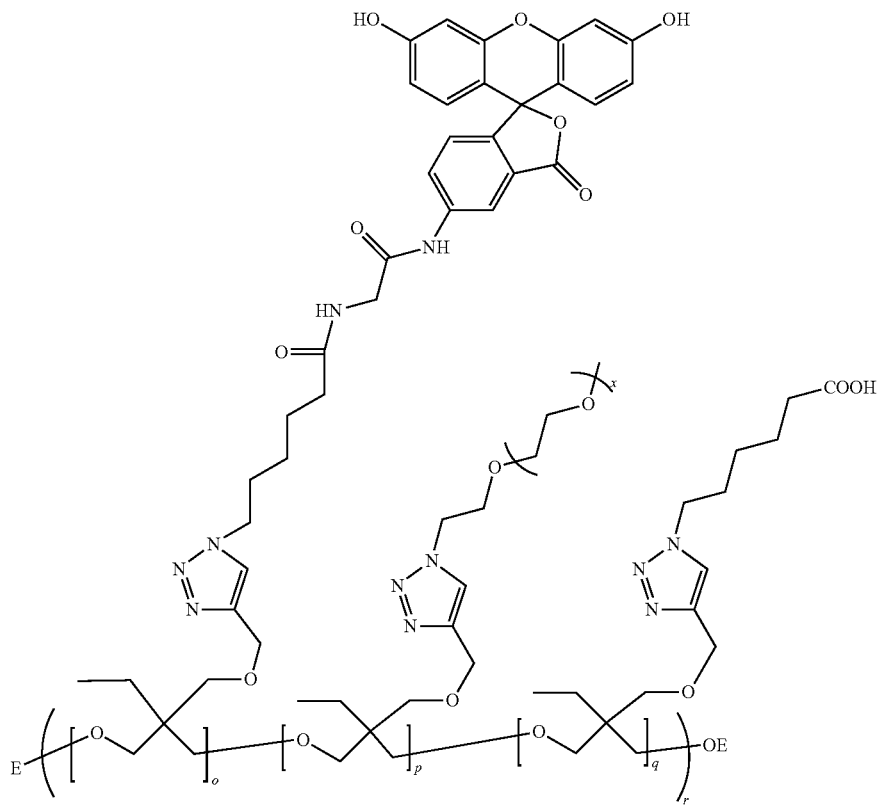
wherein o, p, r and x are greater than 0.

12. The polymer of claim 10, wherein one or more of o, p, q, and r is independently 5-1000; and x is independently 1-100.

13. The polymer of claim 10, wherein one or more of o, p, q, and r is independently 25-120; and x is independently 1-15.

14. The polymer of claim 11, wherein one or more of o, p, q, and r is independently 5-1000; and x is independently 1-100.

15. The polymer of claim 11, wherein one or more of o, p, q, and r is independently 25-120; and x is independently 1-15.

16. The polymer of claim 11, wherein E is hydrogen.

17. A composition, comprising the polymer of claim 5.

18. A polymer, comprising a subunit having the formula:

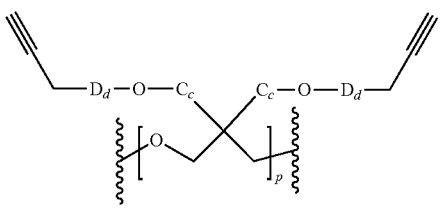

wherein:

C is independently $C_{1-10}$ alkylene, $C_{3-10}$ alkenylene, $C_{3-10}$ alkynylene, $C_{3-20}$ cycloalkylene, $C_{5-20}$ cycloalkenylene, $C_{5-25}$ arylene, —COO—, —C(O)—, —S—, —CONR$^1$—, —NR$^1$—, —CH$_2$CH$_2$O—, —O—, or combination of two or more of the foregoing;

D is independently $C_{1-10}$ alkylene, $C_{3-10}$ alkenylene, $C_{3-10}$ alkynylene, $C_{3-20}$ cycloalkylene, $C_{5-20}$ cycloalkenylene, $C_{5-25}$ arylene, —COO—, —C(O)—, —S—, —CONR$^1$—, —NR$^1$—, —CH$_2$CH$_2$O—, —O—, or combination of two or more of the foregoing;

c is independently 1-20;

d is independently 0-20;

p is greater than 0;

$R^1$ is independently hydrogen, $C_{1-10}$ alkyl, $C_{3-10}$ alkenyl, $C_{3-10}$ alkynyl, $C_{3-20}$ cycloalkyl, $C_{5-20}$ cycloalkenyl, or $C_{5-25}$ aryl;

and wherein one or more of the alkyl, alkenyl, alkynyl, cycloalkyl, cycloalkenyl, aryl, alkylene, alkenylene, alkynylene, cycloalkylene, cycloalkenylene, and arylene may independently be branched, unbranched, unsubstituted, substituted, or contain a hetero atom.

\* \* \* \* \*